United States Patent
Lozano Soto et al.

(10) Patent No.: US 9,445,582 B2
(45) Date of Patent: Sep. 20, 2016

(54) SOLUBLE PROTEIN CD5 OR CD6 FOR THE TREATMENT OF CANCER OR TUMOR OR FOR USE AS AN ADJUVANT

(75) Inventors: Francisco Lozano Soto, Barcelona (ES); Vanessa Gabriela Martinez, Barcelona (ES); Rafael Fenutria Aumesquet, Barcelona (ES)

(73) Assignees: FUNDACIO CLINIC PER A LA RECERCA BIOMEDICA, Barcelona (ES); HOSPITAL CLINIC I PROVINCIAL DE BARCELONA, Barcelona (ES); UNIVERSITAT DE BARCELONA, Barcelona (ES)

( * ) Notice: Subject to any disclaimer, the term of this patent is extended or adjusted under 35 U.S.C. 154(b) by 152 days.

(21) Appl. No.: 14/119,305

(22) PCT Filed: May 29, 2012

(86) PCT No.: PCT/EP2012/059966
§ 371 (c)(1),
(2), (4) Date: Mar. 26, 2014

(87) PCT Pub. No.: WO2012/160215
PCT Pub. Date: Nov. 29, 2012

(65) Prior Publication Data
US 2014/0215644 A1    Jul. 31, 2014

(30) Foreign Application Priority Data

May 26, 2011    (EP) .................................... 11382172

(51) Int. Cl.
| | | |
|---|---|---|
| A61K 38/00 | (2006.01) | |
| A01K 67/027 | (2006.01) | |
| A61K 38/17 | (2006.01) | |
| C07K 14/705 | (2006.01) | |
| A61K 31/475 | (2006.01) | |
| A61K 31/704 | (2006.01) | |
| A61K 39/39 | (2006.01) | |

(52) U.S. Cl.
CPC ....... *A01K 67/0278* (2013.01); *A01K 67/0275* (2013.01); *A61K 31/475* (2013.01); *A61K 31/704* (2013.01); *A61K 38/177* (2013.01); *A61K 39/39* (2013.01); *C07K 14/70596* (2013.01); *A01K 2217/054* (2013.01); *A01K 2217/206* (2013.01); *A01K 2227/105* (2013.01); *A01K 2267/0325* (2013.01); *A01K 2267/0331* (2013.01); *A01K 2267/0387* (2013.01)

(58) Field of Classification Search
None
See application file for complete search history.

(56) References Cited

FOREIGN PATENT DOCUMENTS

| EP | 2143436 A1 | 1/2010 |
|---|---|---|
| WO | WO-2009/153336 A1 | 12/2009 |
| WO | WO-2010/145895 A1 | 12/2010 |

OTHER PUBLICATIONS

Skolnick et al. (Trends in Biotech., 18(1):34-39, 2000).*
Ezzell (J. NIH Res. 1995 7:46).*
Spitler (Cancer Biotherapy, 1995, 10:1-3).*
Boon (Adv. Can. Res. 1992 58:177-210).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987.*
Lin et al Biochemistry USA vol. 14:1559-1563 (1975).*
Abidi, Abbas, et al., "Increased CD6 expression alters [gamma]-IFN responses in CD8+ T-cells independent of TCR repertoire",(2004) *FASEB Journal*, vol. 18, No. 4-5, Abst. 555.7.
Axtell, Robert C., et al., "Cutting edge: Critical role for CD5 in experimental autoimmune encephalomyelitis: inhibition of engagement reverses disease in mice", *The Journal of Immunology*, vol. 173, No. 5, pp. 2928-2932, Sep. 1, 2004.
Chen, X. et al., "CD5 transgenic mice", *FASEB Journal*, vol. 8, No. 4-5, pp. A470, 1994.
Hollander, N., "Immunotherapy of lymphoid and nonlymphoid tumors with monoclonal anti-Lyt-1 antibodies", *The Journal of Immunology*, vol. 133, No. 5, pp. 2801-2805, 1984.
Vera, J., et al., "The CD5 ectodomain interacts with conserved fungal cell wall components and protects from zymosan-induced septic shock-like syndrome", *Proceedings of the National Academy of Sciences of the United States of America*, vol. 106, No. 5, pp. 1506-1511, Feb. 3, 2009.
International Search Report for PCT/EP2012/059966 mailed on Aug. 2, 2012.

* cited by examiner

*Primary Examiner* — Sheela J Huff
(74) *Attorney, Agent, or Firm* — McCarter & English, LLP; Danielle L. Herritt

(57) ABSTRACT

The present invention discloses soluble isoforms of CD5 and CD6, which are scavenger-like lymphocyte receptors, for use in the prophylaxis or therapy of disorders or in therapeutic interventions, which would benefit from an exacerbated immune response to either endogenous or exogenous antigens, resulting from a decrease in lymphocyte subpopulations with regulatory functions and/or increase in lymphocyte subpopulations with effector functions. Special disorders are cell growth disorders, and chronic infections of bacterial, viral, fungal or parasitic origin. The invention also provides animal models for the study and the prophylaxis/treatment of autoimmune diseases, cancer, and chronic infections.

18 Claims, 17 Drawing Sheets

SOLUBLE PROTEIN CD5 OR CD6 FOR THE TREATMENT OF CANCER OR TUMOR OR FOR USE AS AN ADJUVANT

RELATED APPLICATIONS

This application is a 35 U.S.C. §371 national stage filing of International Application No. PCT/EP2012/059966, filed May 29, 2012, which claims the benefit of European Patent Application No. 11382172.2, filed May 26, 2011. The entire contents of each of these applications are explicitly incorporated herein by reference.

The present invention relates to the field of medical approaches for fighting tumours or cancer as well as to adjuvants. These applications share the technical feature of benefiting from enhancement of immune responses against exogenous or endogenous antigens. The invention further provides useful tools to be applied in medicine.

BACKGROUND ART

There are many disorders which would benefit from an enhancement of normal or deficient immune responses through a decrease in the number or the function of lymphocyte subpopulations with regulatory/suppressive function, or through an increase in the numbers or function of effector subpopulations. These disorders include cancers but also some chronic infections of different aetiology (viral, fungal, protozoa, bacterial). Further, it would be beneficial to provide adjuvants, especially in the field of poorly immunogenic antigens.

Cancer or malignant neoplasm are a class of diseases in which a group of cells display uncontrolled growth, invasion that intrudes upon and destroys adjacent tissues, and sometimes metastasis, or spreading to other locations in the body via lymph or blood. These three malignant properties of cancers or malignant neoplasm differentiate them from benign tumours, which do not invade or metastasize.

A tumour is the name for a neoplasm or a solid lesion formed by an abnormal growth of cells (termed neoplastic) which looks like a swelling. Tumour is not synonymous of cancer. A tumour can be benign, pre-malignant or malignant, whereas cancer is by definition malignant.

Tumours and cancers are indeed disorders of normal cell growth (abnormal or uncontrolled).

Many approaches are used to fight cancer and malignant tumours. Cancer can be treated by surgery, chemotherapy, radiation therapy, immunotherapy, monoclonal antibody therapy or other methods. The choice of therapy depends upon the location and grade of the tumour, as well as upon the stage of the disease, and of the patient (age, sex, etc.). Being one of the main causes of worldwide death, several experimental cancer treatments are also under development. Generally, the cancer therapies are also applicable to malignant tumour treatments.

Complete removal of the cancer or tumour without damage to the rest of the body is the goal of the treatment. Sometimes this can be accomplished by surgery, but the propensity of cancers and malignant tumours to invade adjacent tissue or to spread to distant sites by microscopic metastasis, often limits its effectiveness.

In general terms, chemotherapy is the treatment of an ailment by chemicals, especially by killing micro-organisms or cancerous cells. In popular usage, it refers to antineoplastic drugs used to treat cancer. However, chemotherapy involves a drawback as most treatments are also toxic to non-cancerous tissues in the body.

Another therapeutic approach to treat cancer or tumours is by means of immunomodulating agents, which are compounds designed to induce, enhance, or suppress an immune response. Immunotherapies designed to elicit or amplify an immune response are classified as activation immunotherapies. Immunotherapies designed to reduce, suppress or more appropriately direct an existing immune response, as in cases of autoimmunity or allergy, are classified as suppression immunotherapies. The active agents of immunotherapy are collectively called immunomodulators. They include recombinant, synthetic and natural preparations, and are often cytokines.

Finally, monoclonal antibody therapy refers to the use of monoclonal antibodies (mAb) to specifically bind to target cells or soluble molecules. This may then stimulate the patient's immune system to attack or neutralize those cells or molecules. It is possible to create a mAb specific to almost any extracellular/cell surface target, and thus there is a large amount of research and development currently being undergone to create mAb for numerous serious diseases, including cancers. MAb may be used for therapy to destroy malignant tumour cells and prevent tumour growth, for example by blocking specific cell receptors. Sometimes, the mAb is also radioisotopically labelled, which means that once the antibody reaches the target, a lethally radioactive dose is delivered to the target cell.

It is then noteworthy that there is a need for more advanced cell growth disorder therapies and tools to perform them.

The technical problem underlying the present invention can thus be seen as the provision of an immunostimulatory agent, such as for the treatment and/or prophylaxis of tumor and/or cancer as well as adjuvants.

SUMMARY OF THE INVENTION

The present invention provides agents for a specific medical use. The agents may be soluble protein isoforms of CD5 or CD6. Preferably, CD5 is human CD5 and CD6 is human CD6. Polypeptides sharing essentially the same amino acid sequence with CD5 and/or CD6 can also be used as agents of the invention. Embodiments thereof include variants having a polypeptide sequence selected from the following: (a) having 80% or more, preferably 90% or more, more preferably 95% or more, 96% or more, 97% or more, more preferably 98% or more, even more preferably 99% or more identity with SEQ ID NO: 2 or (b) having 80% or more, preferably 90% or more, more preferably 95% or more, 96% or more, 97% or more, more preferably 98% or more, even more preferably 99% or more identity with SEQ ID NO: 3. Even more preferably, the agent of the invention is selected among proteins comprising or consisting of a sequence selected from the group of SEQ ID NO: 2 and SEQ ID NO: 3.

The inventors have surprisingly found that soluble isoforms of the human glycoproteins belonging to the group of scavenger-like lymphocyte receptors display interesting features to be used in therapy. Namely, they are useful as immunomodulatory agents.

Thus the invention aims at a soluble isoform of a scavenger-like lymphocyte receptor for use in the prophylaxis or therapy of disorders or in therapeutical interventions, which would benefit from an exacerbated immune response to either endogenous or exogenous antigens, resulting from a decrease in lymphocyte subpopulations with regulatory functions and/or increase in lymphocyte subpopulations with effector functions.

The medical use according to the invention may be the use in the prophylaxis or therapy of disorders or in therapeutic interventions, which would benefit from an exacerbated immune response to either endogenous or exogenous antigens, resulting from a decrease in lymphocyte subpopulations with regulatory functions and/or increase in lymphocyte subpopulations with effector functions. Particularly, the use may be in the prophylaxis or therapy of cancer or tumour or as an adjuvant.

When the medical use is prophylaxis or treatment of cancer/tumour, the tumour may be selected from a tumour of haematopoietic and a tumour of non-haematopoietic origin.

The use of the agent of the invention as an adjuvant is not limited to particular antigens although administration together with a poorly immunogenic antigen is preferred.

Further, the invention provides a pharmaceutical composition which comprises at least one soluble protein isoform of CD5 or CD6 as defined above and any pharmaceutically acceptable excipient or carrier, for use in the prophylaxis or therapy of cancer or tumour or for use as an adjuvant. Said pharmaceutical composition may comprise at least one further active ingredient. The further active ingredient is selected from the group of chemotherapeutic agents and therapeutic antibodies, and wherein the chemotherapeutic agent may be further preferably selected among a cytostatic and a cytotoxic agent.

The invention also provides non-human animal which expresses a soluble isoform of CD5 or a soluble isoform of CD6. The animal may be a mouse.

In one embodiment thereof, the animal comprises a nucleotide construct comprising SEQ ID NO: 1 coding for an amino acid sequence comprising SEQ ID NO: 2. The inventors have shown that this animal exhibits a phenotype of exacerbated experimentally-induced autoimmune disease and resistance to tumour/cancer progression. It may be preferred that SEQ ID NO: 2 is over-expressed in the animal. In another embodiment, the animal comprises a nucleotide construct coding for CD6. It may be preferred that CD6 is expressed under the lck promoter and the IgH enhancer.

BRIEF DESCRIPTION OF THE DRAWINGS

FIG. 10, panel A shows the levels of IL-6 measured in joint tissue by quantitative PCR (qPCR), and normalized versus GAPDH expression; results are expressed as arbitrary units (A.U.). C stands for control (non-immunized) animals. Panel B shows the levels of antibodies as optical density (OD) at 405 nm of IgG1, IgG2 and total IgG against type II collagen as measured by ELISA in transgenic (square dots) and non-transgenic (circle dots) mice serum at day 0 and week 8 (W8).

DETAILED DESCRIPTION OF THE INVENTION

Terms and Definitions Used Herein

Figure 1:
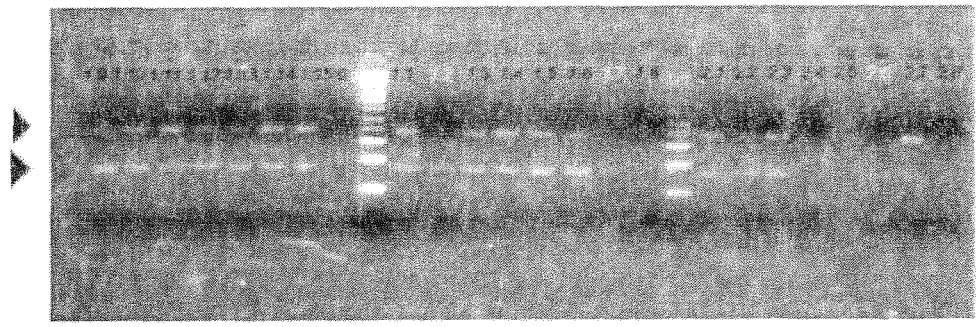
FIG. 1, relating to Example 1, is an image of the agarose gel with the result of PCR amplifications of the nucleotide sequence encoding rshCD5 (SEQ ID NO: 1) from tail DNA. A PCR product encompassing part of the extracellular domains of human CD5 was detected at the expected size (450 base pair, bp) in the transgenic mice (black numbers at upper level of the gel). A fragment of 150 bp corresponding to an exonic region of mouse MHC class II-associated invariant chain (LIEX) gene was also amplified as an internal control for the PCR.

In the sense of the invention, a "cell growth disorder" encompasses any disease or illness which courses with an abnormal, uncontrolled, aberrant or malignant cell growth. This means that the cells grow or divide at a rate higher than normal, and/or that the cells can enter the circulating system (lymph or blood) invading other organs or systems which are not their usual ones (metastasis). Cell growth disorder comprises cancer and/or tumor.

A protein "isoform" means any of several different forms of the same protein. Different forms of a protein may be produced from related genes, or may arise from the same gene by alternative splicing, or by post-translation modifications, such as proteolytic cleavage, phosphorylation, glycosylation, etc. A large number of isoforms are also caused by single-nucleotide polymorphisms or SNPs, small genetic differences between alleles of the same gene. These occur at specific individual nucleotide positions within a gene. Alternatively, isoforms might be generated artificially by conventional molecular biology techniques. Isoform as used herein also includes fragments of a full length protein. For example, a polypeptide having at least 10%, at least 20%, at least 30%, at least 40%, at least 50%, at least 60%, at least 70%, at least 80% or at least 90% of the amino acid sequence of a (e.g. naturally occurring) full-length protein may be termed an isoform of said full-length protein. Examples include the soluble isoforms of CD5 and CD6, respectively, disclosed herein.

Isoform as used herein also includes the concept of glycoform, i.e. protein variants differing (essentially) in their glycosylation pattern.

"Tumour progression resistance" means that a (treated) tumour does not grow and/or metastasize as control (untreated) tumour. Upon treatment, its rate of growth may be slowed down by the treatment. When a tumour grows at a decreased rate, it is implied that a health and aesthetic positive impact ensue due to the success of the treatment.

Throughout the description and claims the word "comprise" and variations of the word typically is not limiting and thus does not exclude other features, which may be for example technical features, additives, components, or steps. However, whenever the word "comprise" is used herein, this also includes a special embodiment in which this word is understood as limiting; in this particular embodiment the word "comprise" has the meaning of the term "consist of".

An "adjuvant" as used herein is a substance that has few or no pharmacological effects by itself, but may increase the efficacy or potency of other agents when given at (essentially) the same time and oftentimes in (essentially) the same route of administration at (essentially) the same site (e.g. injection into the same muscle) as the other agent. More particularly, when used in the context of immunizations, an adjuvant is a substance stimulates or that may stimulate the immune system and increase the response to an immunizing agent, without having any specific antigenic effect in itself. More specifically, an immunologic adjuvant can be defined as a substance that acts to accelerate, prolong, or enhance antigen-specific immune responses when used in combination with specific antigen agent(s).

Agents According to the Invention

The present invention provides a new medical use for CD5 and/or CD6 and isoforms of these proteins. Cluster of differentiation 5 and 6 (CD5 and CD6) are scavenger-like lymphocyte receptors, which are composed of scavenger receptor cysteine-rich (SRCR) domains. The present inventors have surprisingly found that these agents have immunomodulatory properties. Based on this observation, the inventors provide these agents for conditions which would benefit from immunostimulation. Particularly, the inventors provide the use of CD5 and/or CD6 for the treatment or prophylaxis of cancer and/or tumor, as well as adjuvants for immunizations.

Cluster of differentiation 5 (CD5) is a monomeric 67-kDa glycoprotein that acts as an accessory molecule on the surface of lymphocytes. It is expressed on thymocytes from early stages of development, mature peripheral T lymphocytes, and a subpopulation of mature B lymphocytes called B1a. CD5 belongs to the group B of the scavenger receptor cysteine-rich (SRCR) superfamily, an ancient and well conserved group of proteins associated with the immune response. The SRCR group B members include both membrane and secreted proteins involved in the development of immune cells and in the regulation of innate and specific immune responses. Among these there is CD6, a glycoprotein closely related to CD5, with which shares many structural and functional features, as well as a similar tissue expression pattern, since they are mainly lymphoid restricted. Interestingly, the genes coding for CD5 and CD6 map to the same chromosomal region and they are believed to derive from duplication of a common ancestor gene. From here on, they shall be referred to as scavenger-like lymphocyte receptors.

CD5 possesses a relatively large cytoplasmic domain with potential tyrosine and serine/threonine phosphorylation motifs compatible with a function in signal transduction. Indeed, CD5 has been shown to associate with antigen-specific receptors present on T and B cells, thereby modulating T cell receptor (TCR) and B cell receptor (BCR) signalling. Intriguingly, the engagement of CD5 may result in different modulatory signals depending on the cell type analysed and the maturation stage. In mature T cells, CD5 was first considered as a co-stimulator of TCR receptor signalling, but later studies showed a role for this molecule as a negative regulator of TCR signalling in thymocytes and BCR signalling in B1a cells. All these data show the complexity of the processes in which CD5 is directly or indirectly involved.

Although CD5 is a transmembrane molecule, a soluble form of CD5 (shCD5) can be generated in activated T lymphocytes as a result of a proteolytic cleavage (Calvo et al. "Identification of a natural soluble form of human CD5" Tissue Antigens-1999, Vol. 54(2), pp: 128-37). Low levels of shCD5 (picomolar range) have been identified in the serum of healthy human individuals; however, discrete increased expression of this form has been reported in several autoimmune disorders such as rheumatoid arthritis, primary Sjögren's syndrome and atopic dermatitis. The functional relevance of shCD5 has not yet been fully investigated; however, the fact that elevated levels of this protein have been found in certain autoimmune diseases suggests that shCD5 may be an indicator of chronic or exacerbated T cell activation, or alternatively, that it may play a role in the modulation of the immune response by interacting with the still poorly characterized and controversial CD5 ligand/s.

Considering the complex role of CD5 in the immune response, but with the aim of modulating the response by interfering with this molecule and further promoting cancer therapy, some approaches have been developed in which mAb are raised against the T cell differentiation receptor CD5.

The present inventor's finding is surprising in view of the fact that the prior art had pointed in a different direction. For example, Hollander et al. ("Immunotherapy of lymphoid and nonlymphoid tumours with monoclonal anti-Lyt-1 antibodies", The Journal of Immunology—1984, Vol. 133(5), pp.: 2801-2805)) suggest that cross-linking of CD5 by the use of anti-CD5 antibodies have beneficial anti-tumoral effects. They disclose non-cytotoxic anti-Lyt-1 mAb, which have the ability of inhibiting growth of lymphoid and non-lymphoid tumours (lung carcinoma and EL4 leukemia) by means of the interaction of the antibodies with the Lyt-1 receptor, the murine ortholog of the human CD5. The underlying cellular mechanism, i.e. whether the beneficial anti-tumoral effects resulted from either triggering or blocking the CD5 effector functions is still enigmatic.

On the other hand, Axtell et al. ("Cutting Edge: Critical Role for CD5 in Experimental Autoimmune Encephalomyelitis Inhibition of Engagement Reverses Disease in Mice", The Journal of Immunology-2004, Vol. 173, pp.: 2928-2932) describe that in CD5$^{-/-}$ mice the Experimental Allergic Encephalomyelitis (EAE) onset was delayed and attenuated in severity. Axtell et al., conclude that blocking the activity of CD5 is therapeutically beneficial for the treatment of EAE in mice.

Accordingly, the teaching of Axtell et al. leads to the rationale of considering the non-expression or blockade of CD5 as a good way to treat EAE (autoimmune disease). In the CD5$^{-/-}$ mice the autoimmune responses are attenuated, thus, the non-expression or blockade of CD5 would not be a promising strategy to fight cancer. This rationale is the opposite of the teaching in Hollander et al. (supra).

Considering this controversial scenario, it must be further mentioned that by now, little is known about the putative ligand or ligands of CD5. In this regard, Brown et al. in "A Ligand for CD5 Is CD5", *The Journal of Immunology*—2010, Vol. 185, pp.: 6068-6074, propose that CD5 itself is the ligand for CD5. This conclusion is achieved with the results of testing different chimerical soluble proteins containing the sequence of soluble CD5 isoforms from rat, mouse and human, which were allowed to interact with immobilized biotinylated CD5-CD4 fusion proteins. Brown et al. concluded that mouse CD5 reproducibly binds to CD5 from humans, mice, and rats; but human CD5 reacts only with human CD5.

Numerous in vitro experiments have shown that CD5 is a protein capable of modulating signalling through the T cell receptor (TCR) or the B cell receptor (BCR). The development of mice deficient in CD5 revealed that this protein has an overall inhibitory effect on TCR/BCR signalling in vivo, since immune cells isolated from CD5−/− mice were hyperreactive to diverse stimuli ("A role for CD5 in TCR-mediated signal transduction and thymocyte selection" Science 1995, Vol 269(5223), pp.: 535-7). This suggests that impairment of CD5 function in vivo might enhance the immune response through the reduction in TCR/BCR signal inhibition.

Mice deficient in CD5 are a good model for the study of CD5 function, but the findings obtained from this model cannot be directly translatable to the clinic, since inactivation of the gene in patients is nowadays neither feasible nor realistic. A possible way to impair the function of CD5 would then be a blockade of the interactions between membrane-bound CD5 and its ligand/s. Unfortunately, this approach is hindered by the current lack of information regarding CD5 ligand/s: there is an important element of controversy regarding CD5 ligands reported by different groups, such that no group has ever been able to reproduce the results reported by another. Furthermore, no ligand described so far would be able to fully explain the functions of CD5. An alternative approach must then be developed where the interactions between CD5 and its ligand/s might be blocked in a ligand-independent fashion.

Through its ability to bind pathogens, CD5 is considered a scavenger-like lymphocyte receptor, a definition that also applies to CD6, which shares a number of both structural and functional features with CD5 (see above). A soluble form of CD6 (sCD6) has also been previously described (Ramos-Casals et al "High circulating levels of soluble scavenger receptors (sCD5 and sCD6) in patients with primary Sjögren's syndrome" *Rheumatology*—2001 Vol. 40(9), pp.: 1056-1059); although there is virtually no information regarding its physiological function/s, save from the fact that they are able to bind pathogens through an interaction with conserved structures on their surface (pathogen-associated molecular patterns, PAMPs).

CD5 and/or CD6, each alone or both together, will herein be termed "agents of the invention". Preferred embodiments of the agents of the invention are described in the following.

Preferably, CD5 is mammalian CD5, and more preferably human CD5. Preferably, CD6 is mammalian CD6, and more preferably human CD6.

Thus, in a preferred embodiment the agents of the invention are selected from the group consisting of human CD5 and human CD6.

As used herein: preferably, CD5 is a soluble isoform of CD5; preferably, CD6 is a soluble isoform of CD6. Soluble means that the agent of the invention is present in soluble form under physiological conditions, i.e. at physiological pH and physiological ion strength. In a preferred embodiment the soluble isoform consists of the extracellular domain of CD5 or CD6.

Obviously, variants of SEQ ID NO: 2 and SEQ ID NO: 3 to be used as agents according to the present invention include all those inter-individual natural variants or artificially-induced variants. Such variants may include variants representing alterations in the number and type of some amino acids, such as two or three amino acids, as well as an amino acid substitutions (optionally) not altering the global protein 3D-structure, as well as allowing the maintenance of the protein function. The maintenance of the protein function may be tested by systemic and prolonged administration of the exogenous protein derived from SEQ ID NO: 2 or 3 into C57Bl/6 mice, either untreated or subcutaneously implanted with B16 melanoma cells. In the former case, if the number of regulatory T and/or B cells is decreased or the number of effector NKT cells is increased, it is considered that the protein is functional. In the latter case, if the number of tumours and metastases is reduced in relation with an untreated animal, it is considered that the protein is functional. More typically, the protein of the invention is defined by sequence identity with SEQ ID NO: 2 or SEQ ID NO: 3. Embodiments thereof include variants having a polypeptide sequence selected from the following: (a) having 80% or more, preferably 90% or more, more preferably 95% or more, 96% or more, 97% or more, more preferably 98% or more, even more preferably 99% or more identity with SEQ ID NO: 2 or (b) having 80% or more, preferably 90% or more, more preferably 95% or more, 96% or more, 97% or more, more preferably 98% or more, even more preferably 99% or more identity with SEQ ID NO: 3. Even more preferably, the agent of the invention is selected among proteins comprising or consisting of a sequence selected from the group of SEQ ID NO: 2 and SEQ ID NO: 3.

In a more preferred embodiment the agent of the invention comprises or consists of a sequence selected from the group consisting of SEQ ID NO: 2 and SEQ ID NO: 3, being specially preferred SEQ ID NO: 2. Therefore, in a more preferred embodiment the soluble protein isoform of the scavenger-like lymphocyte receptors consists of SEQ ID NO: 2.

SEQ ID NO: 2 corresponds to a mature soluble isoform of human CD5. This mature isoform is the result of a proteolytic process by proteases of an immature protein isoform of human CD5. Said immature isoform comprises SEQ ID NO: 13 and proceeds from the transcription and translation of the nucleotide sequence SEQ ID NO: 1. Once SEQ ID NO: 13 loses the first 24 N-terminal amino acids (or SEQ ID NO: 14), which corresponds to the leader peptide signal sequence, then SEQ ID NO: 2 is obtained. The entire sequence of human CD5 receptor is the one identified with the accession number P06127 (CD5_HUMAN, Last modified Nov. 30, 2010. Version 2 in the UniProtKB/Swiss-Prot database). This sequence corresponds to the receptor in the membrane isoform. Physiologically, the soluble isoform of CD5 is obtained by proteolytical cleavage of the membrane-bound isoform; however, the precise site of cleavage is not known and SEQ ID NO. 2 is obtained by the addition of a stop codon near a putative cleavage site. The stop codon is at position 1180 in relation to the first nucleotide of SEQ ID NO: 1, which is a nucleotide sequence used to express the protein. This stop codon gives rise to a protein having 345 amino acids in its mature (processed) form. That is, once SEQ ID NO 13 (having 369 amino acids) has lost the first 24 N-terminal amino acids or SEQ ID NO: 14. Throughout the description it is indistinctly said that either the amino acid sequence SEQ ID NO: 2 or SEQ ID NO: 13 comes from SEQ ID NO: 1. It is to be understood that inside the cell SEQ ID NO: 13 is finally processed to become SEQ ID NO: 2, thus leading to the mature soluble isoform of human CD5.

SEQ ID NO: 3 corresponds to a mature (fully processed) soluble isoform of human CD6. The sequence of human CD6 receptor is the one identified with the accession number P30203 (CD6_HUMAN, Last modified Dec. 15, 2009. Version 3 in the UniProtKB/Swiss-Prot database). This sequence corresponds to the receptor in the membrane isoform. It has not yet been fully determined if the soluble isoform of CD6 is also generated by proteolytical cleavage; SEQ ID NO. 3 is obtained by the addition of a stop codon in the stalk region that precedes the transmembrane region. Therefore, in another more preferred embodiment the soluble protein isoform of the scavenger-like lymphocyte receptors comprises or consists of SEQ ID NO: 3.

SEQ ID NO: 13, or its mature form SEQ ID NO: 2, and SEQ ID NO: 3 result from the transcription and translation of nucleotide sequences comprising SEQ ID NO: 4 and SEQ ID NO: 5, respectively.

SEQ ID NO: 13, or its mature form SEQ ID NO: 2, and SEQ ID NO: 3 are glycosylated soluble proteins because they are derivatives of glycosylated membrane receptors. Both isoforms (soluble and membrane-bound) of scavenger-like lymphocyte receptors contain putative N- and O-glycosylation motifs. At least some of these motifs are glycosylated as can be deduced from the differences between the predicted and observed molecular weight when a sample is run in an SDS-PAGE electrophoresis gel assay, as well as from the sensitivity to different glycosidases. Nowadays, it remains to be elucidated the specific glycosylation content and type.

Any combination of these preferences is also possible in the present invention, for example CD5 of the invention may be a soluble isoform of human CD5 and CD6 of the invention may be a soluble isoform of human CD6.

It is also possible that the agents of the invention be combined, i.e. that soluble CD5 and soluble CD6 be formulated and/or administered together.

Uses According to the Invention

In a preferred embodiment of the first aspect of the invention, the soluble protein isoform for use in the prophylaxis or immunotherapy of disorders or in therapeutically interventions, which would benefit from an enhancement of normal or deficient immune responses through a decrease in the number or the function of lymphocyte subpopulations with regulatory/suppressive function, or through an increase in the numbers or function of effector subpopulations, is selected from the group consisting of CD5 and CD6. The disorders or therapeutic interventions, which would benefit from an exacerbated immune response to either endogenous or exogenous antigens, are those which would benefit from an enhancement of normal or deficient immune responses, as happens when the numbers and/or the function of lymphocyte subpopulations with regulatory functions is decreased, or when the numbers and/or function of subpopulations with effector function are increased.

These disorders include cell growth disorders or any other disorder which could benefit from reduced numbers and/or function of some lymphocyte subpopulations with well-known regulatory/suppressive function, or from increased numbers and/or function of effector subpopulations. Examples of these are chronic infections of different pathogen origin (bacterial, viral, fungal, or parasitic) in which the normal immune response is insufficient to completely eliminate the pathogen. In the same way, the soluble isoforms could also be useful in therapeutical interventions, which also would benefit from an enhancement of the immune response.

The disorders or therapeutic interventions defined as those "which would benefit from an enhancement of the immune response", are those which can benefit from a decrease in the numbers and/or function of regulatory T and B lymphocyte subpopulations and/or an increase in the numbers and/or function of effector T, B and natural killer (NKT) subpopulations. These T, B and non-T non-B subpopulations may be detected by phenotypical analysis, for example using Fluorescence-activated Cell Sorting (FACS). There are different types of regulatory T cell subpopulations; among these, the present invention focuses on cells characterised by the joint expression of CD4, CD25 and FoxP3, which are called as "Treg" in the present invention. Likewise, there are several different types of regulatory B cell subpopulations, and the present invention focuses on cells characterised by the joint expression of B220, CD1d, CD5 and IL-10, which are referred to as B10 or "Breg" in this invention. In a similar way, the invention focuses on the subpopulation of effector cells which jointly express CD3 and NK1.1, which are called "NKT", and in the subpopulation which jointly expresses B220+IgM$^{high}$ IgD$^{low}$ CD23$^{low}$ CD21$^{high}$ which are called Marginal Zone (MZ) B cells.

As will be illustrated in the examples below, and in the specific case of cell growth disorders (cancer or tumours) the use of soluble, or circulating protein isoforms of the scavenger-like lymphocyte receptors for prophylaxis or therapy of growth disorders implies the unexpected effect of inhibiting tumour and cancer cell growth, and at the same time avoids the metastasis or cell spread from one organ or part of an organ to another non-adjacent organ or part of an organ.

Specific uses of CD5 and CD6 according to the present invention are (1) the use in the prophylaxis or therapy of cancer and/or tumours and (2) the use as adjuvant.

The specific use of the soluble protein isoform of CD5 (exemplified by SEQ ID NO: 2) and CD6 in the prophylaxis or therapy of cancer or tumours is appealing, not only because it significantly lowers the progression of the tumour growth, but also because it reduces the number of metastases. Assuming that CD5 could be the ligand for CD5, it is unexpected that a human isoform would be able to act in a murine model, since this is contrary to what it was previously reported (Brown et al., 2010): human isoforms do not interact with orthologs from other species.

Efforts made in the prior art involving scavenger-like lymphocyte receptors for the treatment of cancer used mAb raised against the CD5 membrane receptor. The evidence in the literature does thus not point to a possible role of soluble isoforms of scavenger-like lymphocyte receptors (CD5 or CD6) in the therapy of cancer. As will be illustrated below, the proposed strategy of the inventors is based on a non-mAb approach involving the use of a soluble form of scavenger-like lymphocyte receptor which is predicted to not cross-link the membrane receptor itself but its ligand/s.

This aspect of the invention could also be formulated as the use of soluble protein isoform of a scavenger-like lymphocyte receptor for use in prophylaxis or the therapy (such as the immunotherapy) of disorders which would benefit from an enhancement of the immune response, cell growth disorders, said cell growth disorders selected from the group consisting of cancer and tumours. In other words and a more concrete manner, the invention elicits a method in which a subject suffering from cancer or malignant tumours is treated with a therapeutically effective amount of a soluble protein isoform of the agent of the invention.

The inventors have further shown that CD5 and CD6 can be used as adjuvant. It can be concluded that CD5 and/or CD6 enhance the effect of an antigen. To that end, the agents of the invention are administered typically together with an antigen. Said antigen may be selected among T-dependent (TD) and T-independent (TI) antigens. Poorly immunogenic antigens are preferred. The agent of the invention is preferably administered together with a poorly immunogenic antigen or non-immunogenic antigen. These antigens include among others molecules of glyco-lipidic nature such as TI type1 (Example 4) antigens of exogenous origin, like the capsular polysaccharide of *Streptococcus pneumoniae*, (polymerized) *Salmonella* flagellin, poly-D-amino acids and lipopolysaccharide, such as for example the *E. coli* lipopolysaccharide; as well as antigens of endogenous origin, such as mucins (colorectal cancer antigens) and other tumoral antigens.

From the data reported herein, it can be deduced that infused soluble human CD5 isoforms do not interact with endogenous mouse CD5 surface receptors, and their putative immunomodulatory effects would not be easily attributed to either blocking or activating the effector functions of endogenously expressed CD5 on mouse lymphocyte subpopulations.

It is also described herein that the soluble protein isoforms of the scavenger-like lymphocyte receptors, preferably human CD5 and human CD6 are used in the prophylaxis or immunotherapy of a disorder selected from the group consisting of cell growth disorders and chronic infections. These disorders share the common pattern of benefiting from an enhancement of normal or deficient immune responses through a decrease in the number or the function of lymphocyte subpopulations with regulatory/suppressive function, or through an increase in the numbers or function of effector subpopulations.

Preferably, they are for use in cell growth disorders selected from the group consisting of cancer and tumours. More preferably, the tumours are of haematopoietic (e.g., leukaemia, lymphoma) or non-haematopoietic origin (e.g., lung carcinoma, melanoma, sarcoma, colon cancer, skin cancer, epithelioma, colorectal cancer, breast cancer, gastric cancer, ovarian cancer, pancreatic cancer, brain cancer, head and neck cancer, oesophageal cancer, testicular cancer, teratoma, cervical cancer).

It may also be preferred that the cancer is selected among immunogenic tumors.

In another preferred embodiment disclosed herein, the chronic infections are selected from the group consisting of viral chronic infections (e.g., B and C hepatitis), protozoal chronic infections (e.g., leishmaniosis, toxoplasmosis), bacterial chronic infections (e.g., tuberculosis, leprosy), and fungal chronic infection (e.g., mucocutaneous candidiasis, cryptococcosis).

Pharmaceutical Composition

A further aspect of the invention relates to a pharmaceutical composition which comprises at least one agent of the invention, and further any pharmaceutically acceptable excipients, for the medical use described above.

A particular thereof relates to is a pharmaceutical composition for use in a combined therapy: To that end, the above pharmaceutical composition further comprises at least one further agent. The type of further agent will naturally be selected according to the intended use. For example, when the pharmaceutical composition is to be used for cancer or tumor therapy, the further agent may be a cancer or tumour therapy agent. On the other hand, when the pharmaceutical composition is to be used for immunization (in that case the agent of the invention is the adjuvant, as highlighted above), the further agent may be an antigen against which immunization is desired. In any case, the further agent may be selected among agents used in conventional and/or currently available therapies.

In a preferred embodiment of the invention, the pharmaceutical composition includes as the scavenger-like lymphocyte receptor one of the soluble protein isoforms of CD5, CD6 or mixtures thereof. Preferably, the scavenger-like lymphocyte receptor is selected from the group consisting of human CD5 and human CD6.

Yet in a more preferred embodiment the pharmaceutical composition includes the scavenger-like lymphocyte receptor selected from the group consisting of SEQ ID NO: 2 and SEQ ID NO: 3 or a combination thereof. Being the most preferred, SEQ ID NO: 2.

Use of Pharmaceutical Composition in Combined Therapy for the Treatment or Prophylaxis of Cancer:

In this embodiment, the pharmaceutical composition may include a cancer or tumour therapy agent that is selected from the group consisting of a radiotherapeutic agent, a chemotherapeutic agent, an immunotherapeutic agent, an antibody and mixtures thereof.

As an example, if the further cancer or tumour therapy agent that is a chemotherapeutic agent, this agent may be selected among all known agents useful for cancer or tumor therapy which are not antibodies. Such agents can oftentimes be subdivided into cytostatic and cytotoxic agents, and either class may be included in the pharmaceutical composition. In particular examples, this agent is selected from from the group consisting of vincristine, doxorubicin, carboplatin, cisplatin, paclitaxel, vinorelbine, gemcitabine, irinotecan, docetaxel, dacarbazine, gefinitib, dasatinib, imatinib, etoposide, cyclophosphamide, and mitoxantrone.

If the pharmaceutical composition comprises an antibody, such antibody may be a monoclonal antibody (mAb). The term monoclonal antibody as used herein also includes humanized and fully human antibodies, as well as variants of antibodies, such as single-chain antibodies, as long as they are monoclonal. In particular cases the monoclonal antibody may be selected from the group of anti-CD20 antibodies and anti-HER2-antibodies. Examples thereof consist of trastuzumab and rituximab.

When used in this embodiment, there may be a positive effect resulting from the combined use as shown in the Examples. Many chemotherapeutic drugs also display immunomodulating effects, and the inventors thus believe that rshCD5 (and also rshCD6) works better with chemotherapy.

In this case, the agent of the invention is used as adjuvant. The further agent to be included in said composition may by an antigen against which immunization is desired. These antigens include among others T-independent type I (TI-1) antigens (Example 4), such as the capsular polysaccharide of *Streptococcus pneumoniae* (preferably polymerized), *Salmonella* flagellin, poly-D-amino acids and lipopolysaccharide from *E. coli*. The antigens also include T-dependent ones (TD) of protein nature, such as for example the bovine collagen type II (Example 2).

Optionally, one or more further adjuvant may also be present in the pharmaceutical composition. The further adjuvant may be selected among known adjuvants, which include inorganic adjuvants such as Aluminium salts, e.g. aluminium phosphate and aluminium hydroxide, as well as organic adjuvants such as squalene or oil-based adjuvants.

The pharmaceutical composition of the invention is a pharmaceutical preparation in which the agent of the invention and the further agent are provided in order to be administered simultaneously; or alternatively administered sequentially.

Animal of the Invention

The invention also provides an animal expressing the agent of the invention in any one or more of the embodiments described under "agent of the invention" above.

Firstly, the inventors hypothesized that transgenic expression or administration of exogenous sCD5 in a mouse model would be able to impair membrane-bound CD5 functions by sequestering natural CD5 ligand/s and disrupt interactions between these proteins. Consequently, the inventors have developed transgenic mice which express a human recombinant form of sCD5 (rshCD5); these mice have been termed rshCD5Tg (Example 1). The phenotype of these mice is very similar to that of non-transgenic mice with respect to gross subpopulation analysis, i.e., rshCD5Tg mice do not display differences in numbers or relative percentages of the major T or B lymphocyte subpopulations (such as CD4+ or CD8+ T lymphocytes), or in lymphocytes at different stages of maturation (such as double negative or double positive T lymphocytes, or pre-B or pro-B cells). However, the inventors' observations have revealed a significant reduction in lymphocyte subpopulations with regulatory/suppressive function, namely T regulatory cells (Treg) and B regulatory cells (Breg), as well as a subpopulation of B cells which normally expresses high levels of membrane CD5 (B1a cells). The decrease in both number and relative percentage in these subpopulations is in line with the expected enhancement of the immune response following impairment of CD5-mediated inhibition of lymphocyte activation. Moreover, a significant increase in NKT cell number has also been observed; NKT are effector cells of the immune system, and their increased number could also result in an enhanced immune response.

Thus, in a preferred embodiment animal comprises SEQ ID NO: 1, and over-expresses a protein comprising SEQ ID NO: 2. The non-human animal is, preferably, a mouse, as described in Example 1.

It is to be noted that the mouse over-expressing the soluble isoform of CD5 (SEQ ID NO: 2) exhibits a phenotype correlating with an exacerbated form of well-established experimentally-induced autoimmune diseases, such as CIA and EAE.

Moreover, the mouse represents an interesting tool to assay adjuvant therapies for use in cancer and malignant tumours, namely for testing the effect of multiple compounds co-administered with human soluble CD5 (over-expressed in the transgenic non-human animal).

Additionally, as will be illustrated in the examples, the modulation of the murine immune system by the soluble isoform of human CD5 also resulted in B16 melanoma tumours growing more slowly in the transgenic mice as compared to non-transgenic littermates. Furthermore, exogenous administration of the soluble isoform of human CD5 also delayed cancer progression in combination with chemotherapy, as compared to the effectiveness of chemotherapy alone. Thus, all these data support a role for the interactions between CD5 and its ligand/s (generically named CD5L) in the homeostasis of regulatory and effector cell pools, while surprisingly focusing the use of soluble human CD5 as adjuvant in cancer and tumour therapy, but also in chronic infectious disorders or therapeutical interventions both benefiting from exacerbated immune responses to endogenous or exogenous antigens.

In view of the results obtained with the transgenic mice over-expressing soluble human CD5, or with the exogenous administration of this protein, it seems proper to conclude that this soluble isoform modulates the response of the immune system in a different way than that of the antibodies raised against the membrane receptor or other chimeric Fc proteins containing CD5.

In a preferred embodiment, the cell growth disorder is a cancer. More preferably, the cell growth disorder (cancer) is selected from melanoma, sarcoma, colon cancer, skin cancer, epithelioma, colorectal cancer, breast cancer, gastric cancer, ovarian cancer, pancreatic cancer, brain cancer, head and neck cancer, oesophageal cancer, testicular cancer, teratoma, cervical cancer This aspect of the invention relates to a genetically modified non-human animal which comprises a nucleotide construction comprising SEQ ID NO: 1 encoding an amino acid sequence comprising SEQ ID NO: 2, and wherein the non-human animal exhibits a phenotype of exacerbated experimentally-induced autoimmune disease and resistance to tumour/cancer progression.

The non-human transgenic animal which comprises SEQ ID NO: 1 expresses the soluble isoform of a human scavenger-like lymphocyte receptor (rshCD5 or SEQ ID NO: 2), and it does show decreased numbers of lymphoid subsets with reported regulatory functions (decreased proportion of T regulatory (Treg) and B regulatory (Breg) cells), and increased numbers of lymphoid subsets with effector function (MZ B-cells, NKT cells). This non-human transgenic animal does not spontaneously develop any evident autoimmune disorder, but it shows exacerbated autoimmune responses when experimentally induced. Moreover, the non-human transgenic animal shows increased resistance to the progression of tumours compared to their non-transgenic littermates. In fact, if tumour development is induced (i.e., by injection of B16 cells), the tumours grow at a slower rate and, surprisingly, their capacity to metastasize is reduced. This non-human transgenic animal also shows an increased immune response to immunization with T-independent antigens (such as with trinitrophenylated derivatives of lipopolysaccharide (TNP-LPS)).

Interestingly, when purified soluble scavenger-like lymphocyte receptor protein (SEQ ID NO:2) was exogenously administered to wild-type non-transgenic animals on alternate days for a two week period of time they showed the same lymphocyte subset alterations than those above reported for transgenic animals (decreased is proportion of Treg and Breg cells, and increased proportion of NKT). Similarly, wild-type mice treated with rshCD5 in combination with chemotherapy showed slower tumour growth than mice treated with chemotherapy alone.

CD6 is a receptor closely related to CD5, with which it shares a high degree of homology, both structural and functional. CD6, like CD5, is also expressed as a membrane-bound form on lymphocytes, where it contributes to the formation of the immune synapse. A soluble form of CD6 can also be detected in the circulation, much as it happens with CD5; exogenous administration of a recombinant form of human soluble CD6 (rshCD6) to wild-type mice also resulted in phenotypical alterations in subpopulations with regulatory/suppressive function (data not shown). The inventors thus secondly hypothesized that transgenic expression or administration of exogenous sCD6 in a mouse model could further support the findings of the present invention. Consequently, the inventors have developed transgenic mice which express a human recombinant form of sCD6 (rshCD6); these mice have been termed rshCD6Ick (Example 7). The invention thus also particularly relates to a non-human animal expressing CD6. An example thereof is provided in Example 7. Any form or variant of CD6 may be expressed, but particularly preferred are soluble variants and/or human variants of CD6, and various embodiments thereof are given above under "agents of the invention".

The CD6 detailed above may in the transgenic animal be expressed under the control of any promoter; however it may be preferred to express CD6 particularly or preferably or exclusively in cells of the immune system, such as in T cells and/or B cells. It may be preferred that the CD6 is expressed essentially only in T cells, or that the CD6 is expressed essentially only in B cells and T cells, or that the CD6 is expressed essentially only in any cells of the immune system. Essentially only means that the expression levels of the CD6 in the respective cells are at least 100% higher than in control cells, at least at least 200% higher than in control cells, at least 500% higher than in control cells or at least 1000% higher than in control cells, or that expression of CD6 is not detectable in the control cells. Any cell or tissue of the same animal may be used as defined control cells, for example taken from liver or muscle.

For the purpose of this aspect of the invention, the CD6 may be expressed under the control of a promoter allowing for particular or exclusive expression in those cells. The skilled person can chose among any known promoter with such properties; in a particular embodiment, the promoter is the Ick promoter, as described in Example 7. It may also be preferred to use the IgH enhancer (Eμ). The latter is intended to drive the expression of rshCD6 preferentially to B lymphocytes. Most preferably, the CD6 expressed by the mouse is represented by SEQ ID NO: 3.

Figure 18:
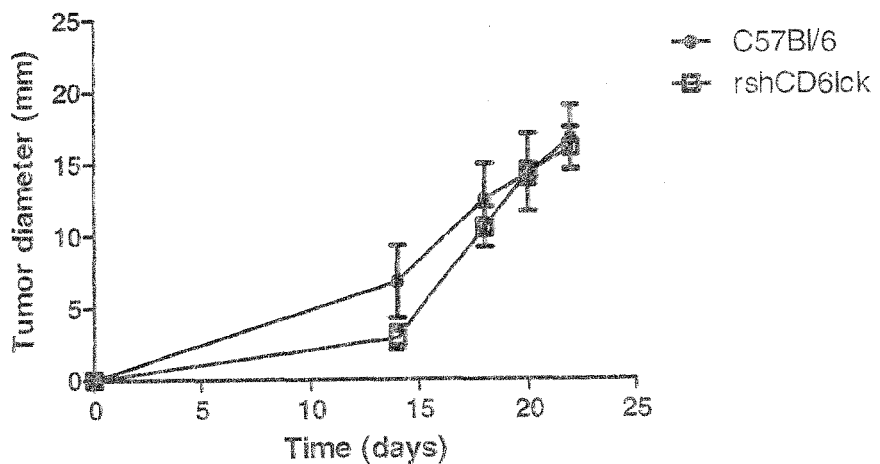
FIG. 18, related to Example 6, is an analysis of the role of rshCD6 in tumor growth. (A) $1 \times 10^5$ B16 melanoma cells were injected s.c. in the dorsal area of rshCD6Ick transgenic mice or in non-transgenic C57Bl/6 mice (n=5 per group). Tumor growth was monitored three times a week with a Vernier calliper. (B) $1 \times 10^5$ B16 cells were injected s.c. in the dorsal area of C57Bl/6 mice (n=5 per group). Mice were treated with vehicle or rshCD6 (25 μg) i.p. every 48 hs starting at the day of tumor injection. Chemotherapy (vincristine 1 mg/kg, doxorubicin 3.3 mg/kg) was administered i.p. on day 3 post-tumor injection. (C) $1 \times 10^5$ RMA-S lymphoma cells were injected s.c. in the dorsal area of C57Bl/6 mice (n=5 per group). Mice were treated with vehicle or rshCD6 (25 μg) i.p. every 48 hs starting at the day of tumor injection. Chemotherapy (doxorubicin 3.3 mg/kg) was administered i.p. on days 5 and 12 post-tumor injection.
Figure 18:
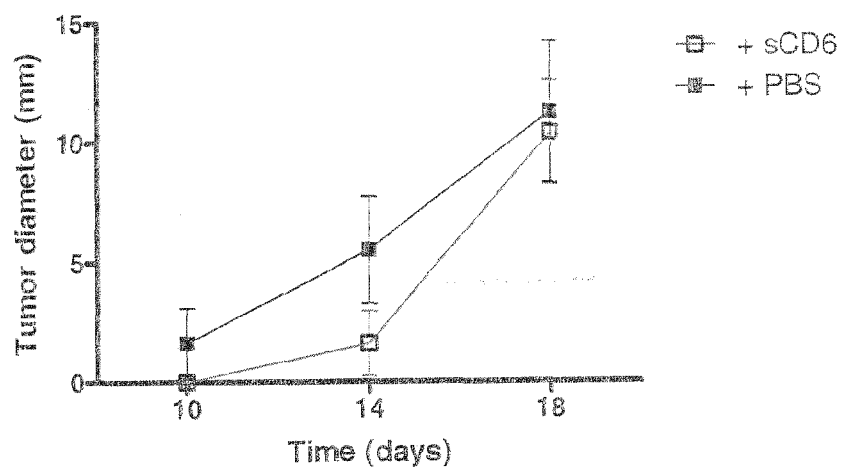
Figure 18:
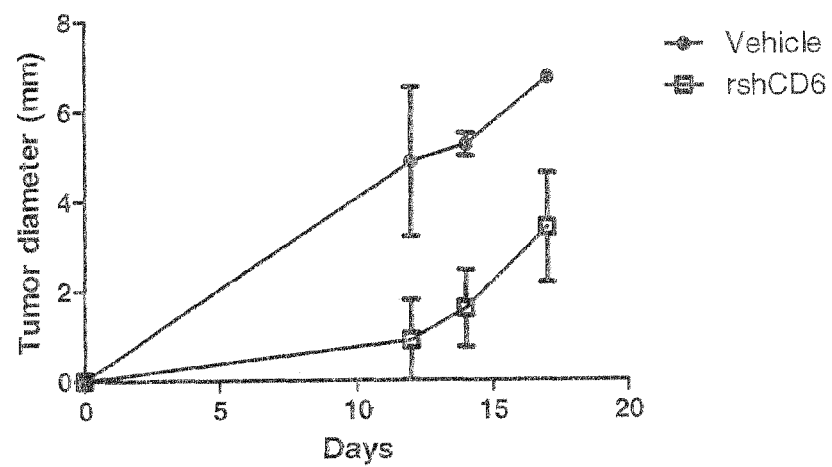

Using the mouse of the invention, a possible immunomodulating effect of recombinant soluble human CD6 in the anti-tumor response was evaluated. This is detailed in Example 6. Transgenic mice expressing rshCD6 under the control of the lymphocyte specific promoter Ick and the IgH enhancer (Eμ) were used for these studies (rshCD6Ick mice, see Example 7). These mice express rshCD6 preferentially in T but also in B lymphocytes, much as is the case with the endogenous protein, and levels are expected to be high. As shown in FIG. 18, after injection of various tumor cell types, rshCD6Ick mice displayed a slightly slower tumor growth rate when compared to non-transgenic mice.

The animal of the invention may be obtained by any method suitable for that purpose. Particularly in the case of a mouse, this may be done for example by a) obtaining a nucleotide construct coding for the agent of the invention to be expressed; b) microinjecting the construct of step a) in the pronucleus of a fertilized ovule; c) culturing the fertilized ovule; d) transplanting the ovule to a pseudopregnant mouse female; and e) selecting from the progeny those animals containing cDNA encoding the agent of the invention.

Non-Medical Method

The animals of the invention are also a useful tool for use in non-medical methods of the invention:

The present invention encompasses a non-medical experimental method for increasing the severity of autoimmune disease and/or tumour progression resistance in an organism which expresses the agent of the invention. A particular example thereof is the non-human animal in which the construct that encodes for SEQ ID NO: 2 is over-expressed. Another example is the non-human animal expressing soluble CD6, such as represented by SEQ ID NO: 3.

EXAMPLES

The following examples and drawings are provided by way of illustration, and they are not intended to be limiting of the present invention. Furthermore, the present invention covers all possible combinations of particular and preferred embodiments described herein.

Example 1

Generation of rshCD5Tg Transgenic Mice (Mice Over-Expressing SEQ ID NO: 2 or Human Soluble CD5 Isoform)

In an attempt to investigate the functional relevance of shCD5 in vivo, the inventors generated a new strain of mice which expressed recombinant shCD5 (rshCD5, also named SEQ ID NO: 2) under the control of the SV40 promoter (SEQ ID NO: 10) and the IgH enhancer (Eμ). The latter is intended to drive the expression of rshCD5 preferentially to B lymphocytes.

Construction for expression of recombinant human soluble CD5 isoform was done following the methodology disclosed by Calvo et al. "Interaction of recombinant and natural soluble CD5 forms with alternative cell surface ligand", *Eur. J. Immunol.*—1999, Vol. 29, pp.: 2119-2129. The methodology includes the construction by EcoRI/KpnI cloning of two previously reported cDNA clones, pT1-1 and pT1-2 into the EcoRI site of a modified version of the pHβAPr-1-neo expression vector. These two clones are disclosed by Jones et al., in "Isolation of complementary DNA clones encoding the human lymphocyte glycoprotein T1/Leu-1", *Nature*—1986, Vol. 323, pp.: 346-349. The introduction of SEQ ID NO: 1, encoding for a soluble isoform of human CD5 was introduced into the pHβAPr-1-neo expression vector. This step was performed as reported in Gunning et al., "A human β-actin expression vector system directs high-level accumulation of antisense transcripts", *Proc. natl. Acad. Sci. USA.*—1987, Vol. 84, pp.: 4831-4835. For generation of a soluble human CD5 form, the pT1-2 was cloned into M13mp18 as an EcoRI/EcoRI fragment and then subjected to oligonucleotide directed mutagenesis to introduce the premature stop codon at P346, which in turn created a new MseI enzyme restriction site. In fact, the stop codon P346 is named in relation to the mature protein when the 24 amino acids corresponding to the leader sequence at the N-terminal of the immature protein are lost.

Figure 19:
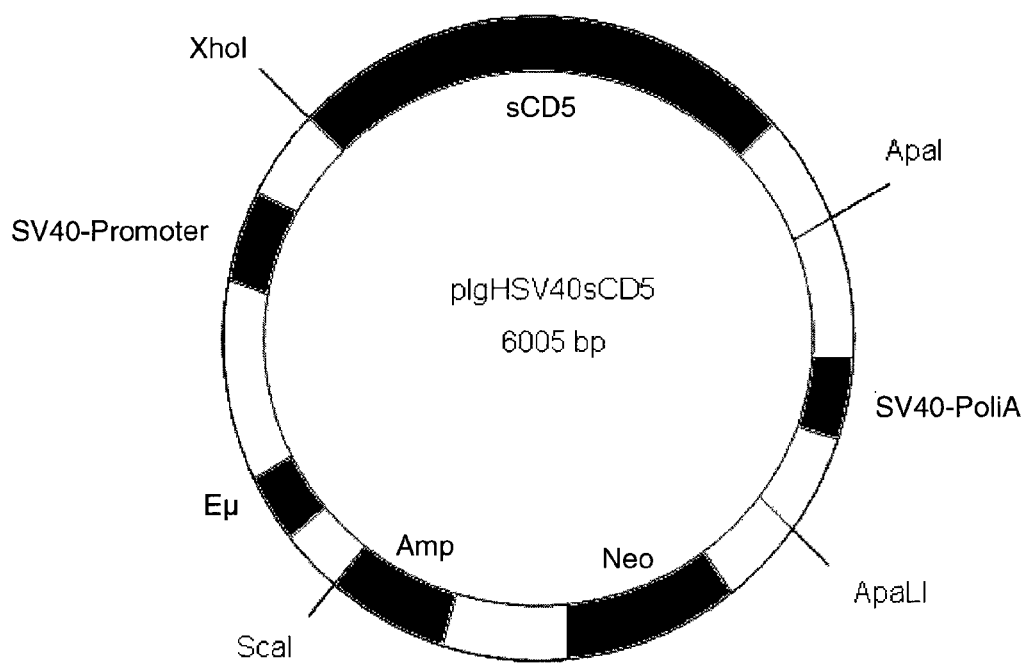
FIG. 19 is a schematic drawing of the expression vector construction for expressing human recombinant soluble protein CD5 (rshCD5 or SEQ ID NO: 2). sCD5 means SEQ ID NO: 1; Amp is the gene giving resistance to ampicillin; Neo is the gene giving resistance to neomycin; ScaI, XhoI, ApaI, ApaLI are the sites of restriction endonucleases; SV40-Promoter is the sequence encoding the SV40 promoter or SEQ ID NO: 10; Eμ is the sequence encoding the Eμ enhancer; SV40-Poli A is a sequence encoding a polyadenylation signal from the Simian Virus 40 (SV40 virus), pIgHSV40sCD5 is the expression vector to produce rshCD5 or SEQ ID NO: 2.

Complementary DNA fragments encoding rshCD5 (SEQ ID NO: 2) were obtained by PCR using the pHβAPr-1-neo/CD5.P346$^{STOP}$ as a template (Calvo et al. "Interaction of recombinant and natural soluble CD5 forms with alternative cell surface ligand", *Eur. J. Immunol.*—1999, Vol. 29, pp.: 2119-2129) and cloned into an expression plasmid containing the Eµ enhancer and the SV40 promoter. This plasmid was identified as pIgHSV40sCD5 as can be seen in FIG. 19.

The pIgHSV40sCD5 construction was linearized by restriction enzyme digestion, gel-purified, and microinjected, using standard protocols, into mice one-cell states fertilized embryos, obtained from C57BL/6J×SJL/J (B6SJL F2) superovulating females.

The obtention of the non-human mice of the invention is thus performed by a) obtaining the construction comprising SEQ ID NO: 1; b) microinjecting the construction of step a) in the pronucleus of a fertilized ovule; c) culturing the fertilized ovule; d) transplanting the ovule to a pseudopregnant mouse female; and e) selecting from the progeny those animals containing cDNA encoding SEQ ID NO: 2 or (rshCD5).

To identify the transgenic mice, a PCR from tail or ear DNA was performed using the forward primer of SEQ ID NO: 6 (5'-GCTGTCCCAGTGCCACGAACT-3'), and reverse primer of SEQ ID NO: 7 (5'-GAAGCTCCTCTGT-GTCCTCAT-3'), which are specific for the extracellular region of human CD5. FIG. 1 shows a representative PCR analysis showing the expected 450 bp band which identifies the transgenic DNA; the 150 bp band corresponds to an internal PCR amplification control from the house-keeping LIEX gene by using the forward primer of SEQ ID NO: 8 (5'-TCACTCAAGGCAACCTT CCTGC-3'), and reverse primer of SEQ ID NO: 9 (5'-CGACCTCATCTCTAACCAT-GAACAG-3'). In this experiment, mice 1.2 and 1.7 are non-transgenic littermates, while the rest of the mice are positive for the rshCD5 transgene.

Figure 2:
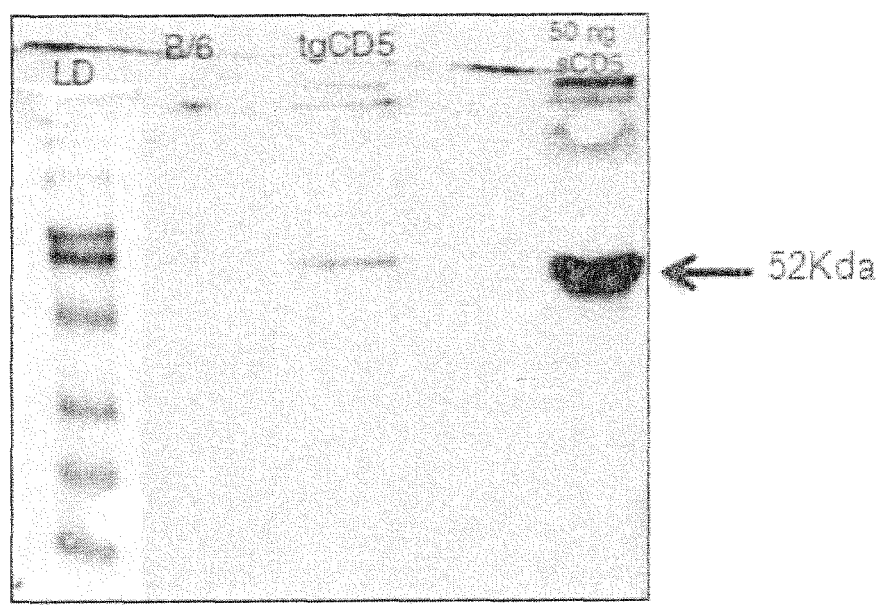
FIG. 2, relating to Example 1, is the image of a Western blot analysis of pooled sera from wild-type non-transgenic C57BL/6 mice (B/6) and transgenic rshCD5Tg mice (tgCD5) over-expressing SEQ ID NO: 2. The further right lane contains 50 ng of affinity-purified rshCD5 as a positive control. rshCD5 (SEQ ID NO: 2) was immunoprecipitated from pooled mouse sera using the anti-human CD5 Cris-1 mAb coupled to CNBr-activated Sepharose beads. Immunecomplexes were then analyzed by Western blotting using the anti-human CD5 mAb Leu-1 and horseradish peroxidase (HRP)-labelled goat anti-mouse 1 g. Molecular weight standards are indicated to the left of the panel. LD is the molecular weight standards lane.

To confirm expression of rshCD5 (SEQ ID NO: 2), pooled sera from transgenic rshCD5tg mice or their non-transgenic littermates (n=5 for each group) were immunoprecipitated with an anti-human CD5 mouse mAb (Cris-1, Alberola-Ila et al. "Intracellular events involved in CD5-induced human T cell activation and proliferation" *The Journal of Immunology*—1992, Vol. 148(5), pp: 1287-1293) and the immune complexes resolved in 10% SDS-PAGE, followed by Western blotting with a rabbit polyclonal antiserum raised against the extracellular region of hCD5. As shown in FIG. 2, the blot shows a 52-kDa band in rshCD5tg serum (tgCD5 lane), which was absent from the sera of non-transgenic littermates.

Transgenic expression of rshCD5 was expected to be produced from birth, and thus transgenic mice should be tolerant to this human protein. To confirm a lack of response to exogenously administered rshCD5, the inventors investigated the presence of anti hCD5-antibodies in transgenic rshCD5tg mice immunized with either rshCD5 or with rshCD6 as a control. Two consecutive fortnightly immunizations (25 µg each rshCD5 or rshCD6) in complete (CFA) and incomplete (IFA) Freund's adjuvant, respectively, were performed, and four weeks after the first immunization sera were collected and analyzed for anti-rshCD5 or anti-rshCD6 reactivity by ELISA, using bovine serum albumin (BSA), rshCD5 and rshCD6 as coating proteins. In the group of rshCD5tg immunized with rshCD5, mouse sera showed very low antibody titers against rshCD5 as measured by OD, as compared to wild-type mouse sera. In contrast, both transgenic rshCD5tg mice and wild-type non-transgenic mice immunized with rshCD6 showed similarly high titers of anti-rshCD6 antibodies; as a negative control, BSA-immunized mice showed no detectable levels of specific Igs against rshCD5 or rshCD6 (data not shown). These results support the notion that exogenous rshCD5, but not rshCD6, is poorly immunogenic to transgenic rshCD5tg mice, as expected.

Example 2

Figure 3:
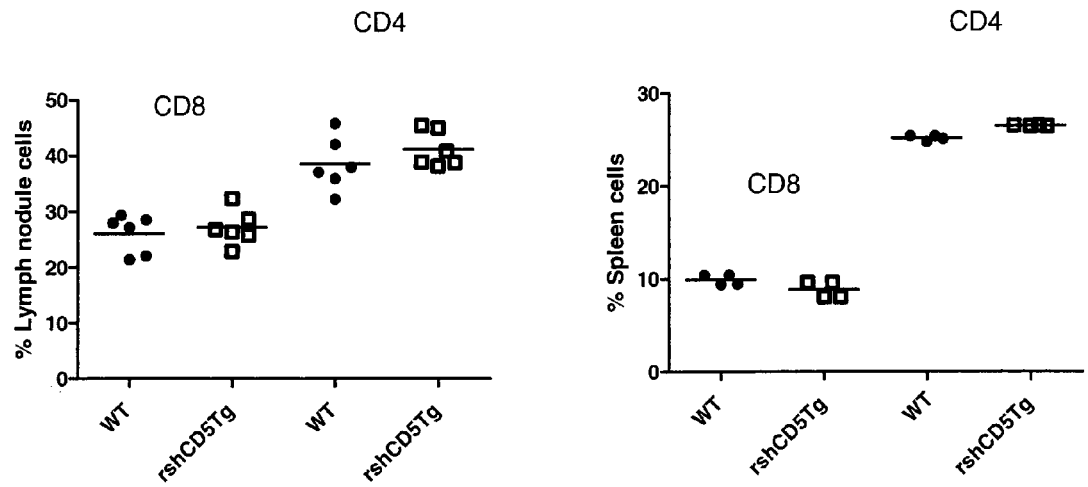
FIG. 3, relating to Example 2, shows the result of a flow cytometry analysis of peripheral T lymphocyte subpopulations in transgenic rshCD5Tg mice (square spots) with respect to wild type (wt or circles) non-transgenic mice. Namely, the image shows the percentages of single positive (CD4+ or CD8+) T cells in lymph node (LNC) and spleen (SC). The data proceed from an assay wherein the lymph node cells and the spleen cells were stained with anti-CD3, anti-CD4 and anti-CD8 specific mAbs to identify CD4+, CD8+, CD4+CD8+ or CD4−CD8− cells.
Figure 4:
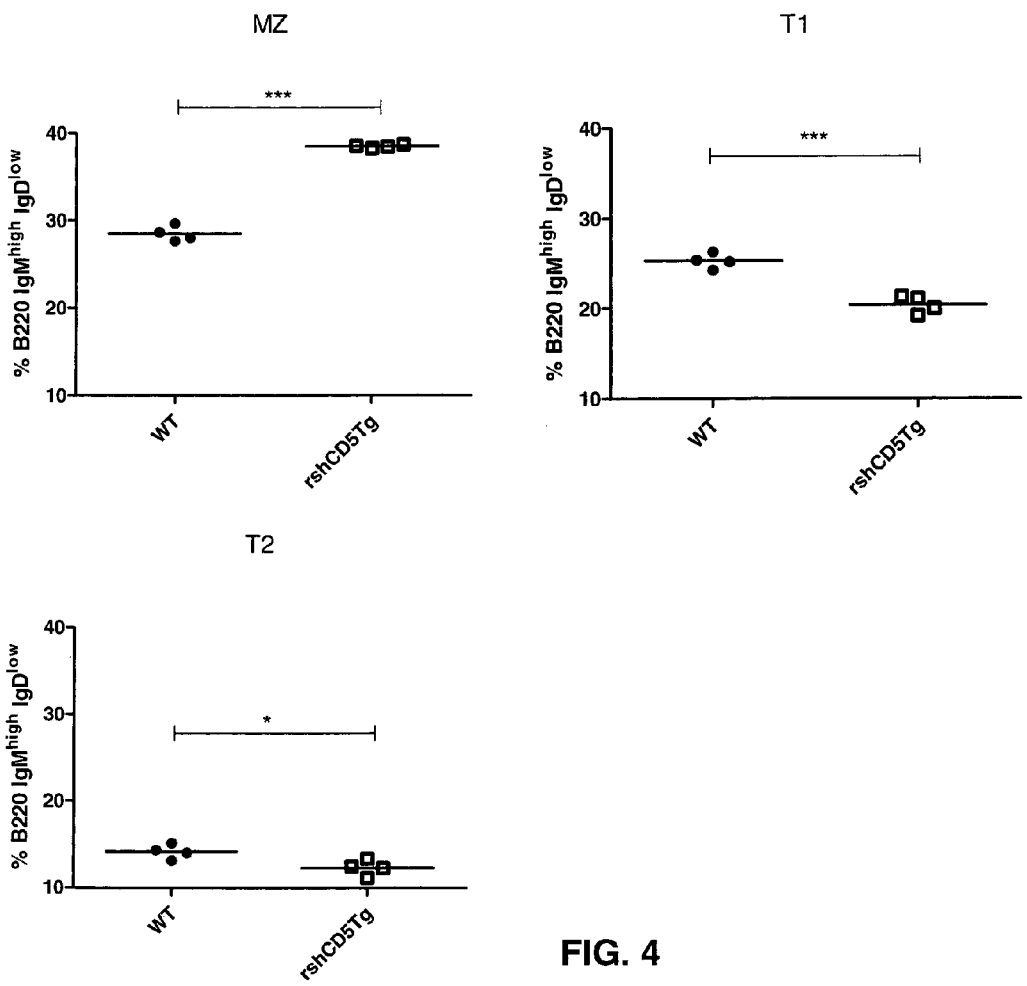
FIG. 4, relating to Example 2, shows the result of a flow cytometry analysis of B lymphocyte subpopulations in transgenic rshCD5tg (square dots) and non-transgenic mice (wt or circle dots). Spleen cells were stained with mAbs directed against IgM, IgD, B220, CD23 and CD93/AA4 to distinguish between transitional 1 (T1), transitional 2 (T2) and marginal zone (MZ) cells.

Concomitantly Reduced Proportion of Lymphocyte Subpopulations with Well-Known Regulatory Function and Exacerbated Autoimmune Responses in Transgenic rshCD5tg Mice To investigate the effect of rshCD5 in T cell development and homeostasis, the inventors analyzed the major subpopulations of T cells in the thymus, lymph node and spleen of transgenic rshCD5tg mice and their non-transgenic littermates. Total cell numbers and percentages of CD4+ and CD8+ T lymphocytes were not significantly different in the thymus, lymph node or spleen of transgenic mice as compared to non-transgenic littermates (data not shown). Further analysis of the major T and B cell populations from bone marrow, lymph node and thymus by flow cytometry did not detect any gross phenotypic abnormalities in transgenic rshCD5tg mice as compared to non-transgenic littermates. These data are retrieved in FIG. 3 and FIG. 4, wherein flow cytometry analysis of different T and B cell subpopulations is depicted. Flow cytometry was performed with a FACS Canto I flow cytometer (BD Biosciences, USA). Significant differences were observed in the percentage (see FIG. 3) or absolute numbers (not shown) of major (CD4+ or CD8+) T-lymphocyte subpopulations in the lymph and spleen of transgenic rshCD5tg mice as compared to non-transgenic mice (wt).

To analyze the effect of rshCD5 in B lymphocyte development, bone marrow cells were stained with a series of antibodies (CD43, B220, CD24 and BP-1) to identify the different B cell subsets at various stages of maturation. From the gated CD43+B220+ subpopulation, pre-pro-B cells, early pro-B cells, late pro-B cells and pre-B cells could be identified based on the expression of CD24 and BP1 (data not shown). No significant differences were observed in B cell subsets in the bone marrow of rshCD5tg mice, suggesting that no major alterations occur during bone marrow B cell development in transgenic mice.

Although no major differences in bone marrow B cell populations were observed, the inventors also analyzed peripheral B cell subsets from spleen. To analyze peripheral B cell subsets, the gating strategy used was adapted from Cariappa et al "The recirculating B cell pool contains two functionally distinct, long-lived, post-transitional, follicular B cell populations", *Journal of Immunology*—2007, Vol. 179(4), pp.: 2270-2281. Gated on $IgM^{high}$ $IgD^{low}$, transitional 1 (T1), transitional 2 (T2) and marginal zone (MZ) B cells can be distinguished based on their differential expression of the surface markers CD23 and CD93/AA4. On the other hand, transitional 3 (T3) and follicular I (POLI) cells can be distinguished in the $IgM^{low}$ $IgD^{high}$ gated subpopulation using the CD21/35 and CD93/AA4 markers. Finally, the $IgM^{high}$ $IgD^{low}$ gated subpopulation allows for the detection of follicular II (FOLII) cells and marginal zone precursors (MZP) based on the surface expression of CD93/AA4 and CD21/35. A significant decrease in the percentage of the T1 subpopulation as well as an increase in MZ cells was detected in transgenic rshCD5tg mice as compared to non-transgenic littermates. These results are directly derivable from FIG. 4, wherein the percentage of B220+ subpopulation cells (gated on $IgM^{high}$ $IgD^{low}$) is depicted for MZ, T1 and T2. These results are of clinical relevance due to the well-known functional importance of splenic MZ B cells in the response to thymus independent (TI) antigens, such as bacterial capsular polysaccharide antigens.

Figure 5:
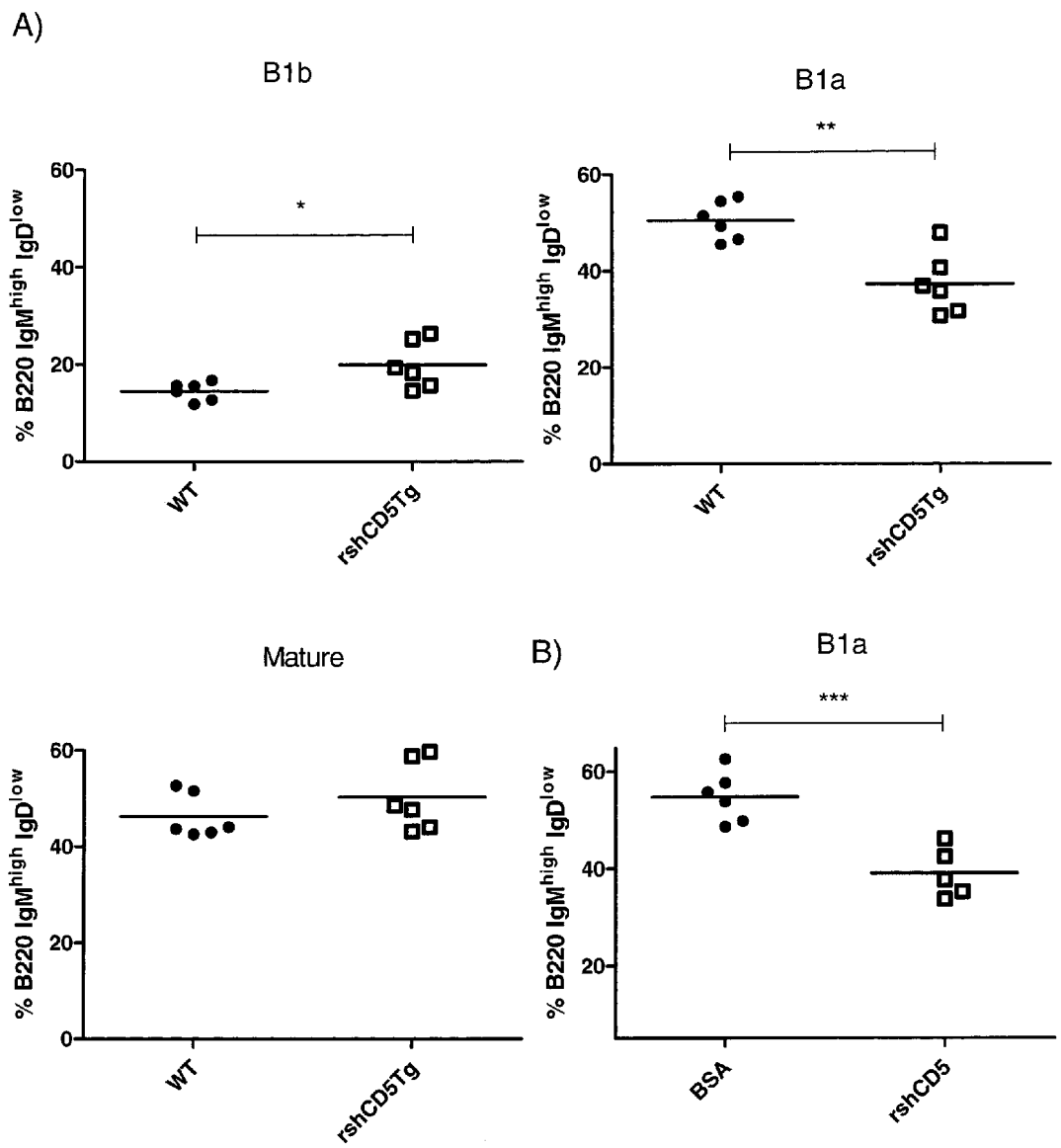
FIG. 5, relating to Example 2, shows in panel A the different proportions of B1b, B1a and mature B cells (M) in peritoneal lavage samples from transgenic rshCD5tg (squares) and non-transgenic mice (wt or circles), identified by staining with mAbs against B220, IgM, IgD and CD5. Panel B shows the change in B1a cells caused by exogenous administration of rshCD5 to wild-type non-transgenic C57Bl/6 mice. shrCD5 means soluble human recombinant CD5 (which is SEQ ID NO:2). shrCD5 and rshCD5 are used in the present invention as synonymous.

Since the CD5+ subpopulation of B lymphocytes (B1a) is enriched in the peritoneal cavity the inventors hypothesized that it might be affected by the presence of circulating levels of rshCD5. The peritoneal B cells were analyzed by means of staining for IgM and IgD, and also for CD5 to distinguish between the B1a (CD5+ B220$^{low}$) and B1b (CD5−B220$^{high}$) subpopulations. Analysis of CD5 expression on the B220+ population showed a significant decrease in the percentage of B1a cells (B220+ CD5+) and a slight increase in the percentage of B1b cells (B220+ CD5−). These data are depicted in FIG. 5, panel A. Interestingly, the decrease in B1a cells was also observed in non-transgenic wild-type mice (wt) treated with exogenous rshCD5 (SEQ ID NO:2) for two weeks at alternate days, as derivable from FIG. 5, panel B.

CD5 signalling is required for the homeostasis of and IL-10 production by peritoneal B1a cells, and it is believed that rshCD5 might interfere with putative ligand binding of endogenous CD5 expressed on the surface of developing B lymphocytes. Thus, the inventors assayed if B regulatory cell subpopulations might be altered in the presence of increased circulating levels of rshCD5.

Among the IL-10 producing B cell subpopulations with reported regulatory function are CD5-positive and CD5-negative ones. The former include both peritoneal B1a cells (B220+ CD5+) and a recently reported spleen B cell subset named B10 cells. These IL-10 producing B cells (B10 B cells) display a unique CD5+ CD1d$^{high}$ phenotype, and represent only 1-2% of splenic B cells; however, this subpopulation is highly enriched in the peritoneal cavity.

Figure 6:
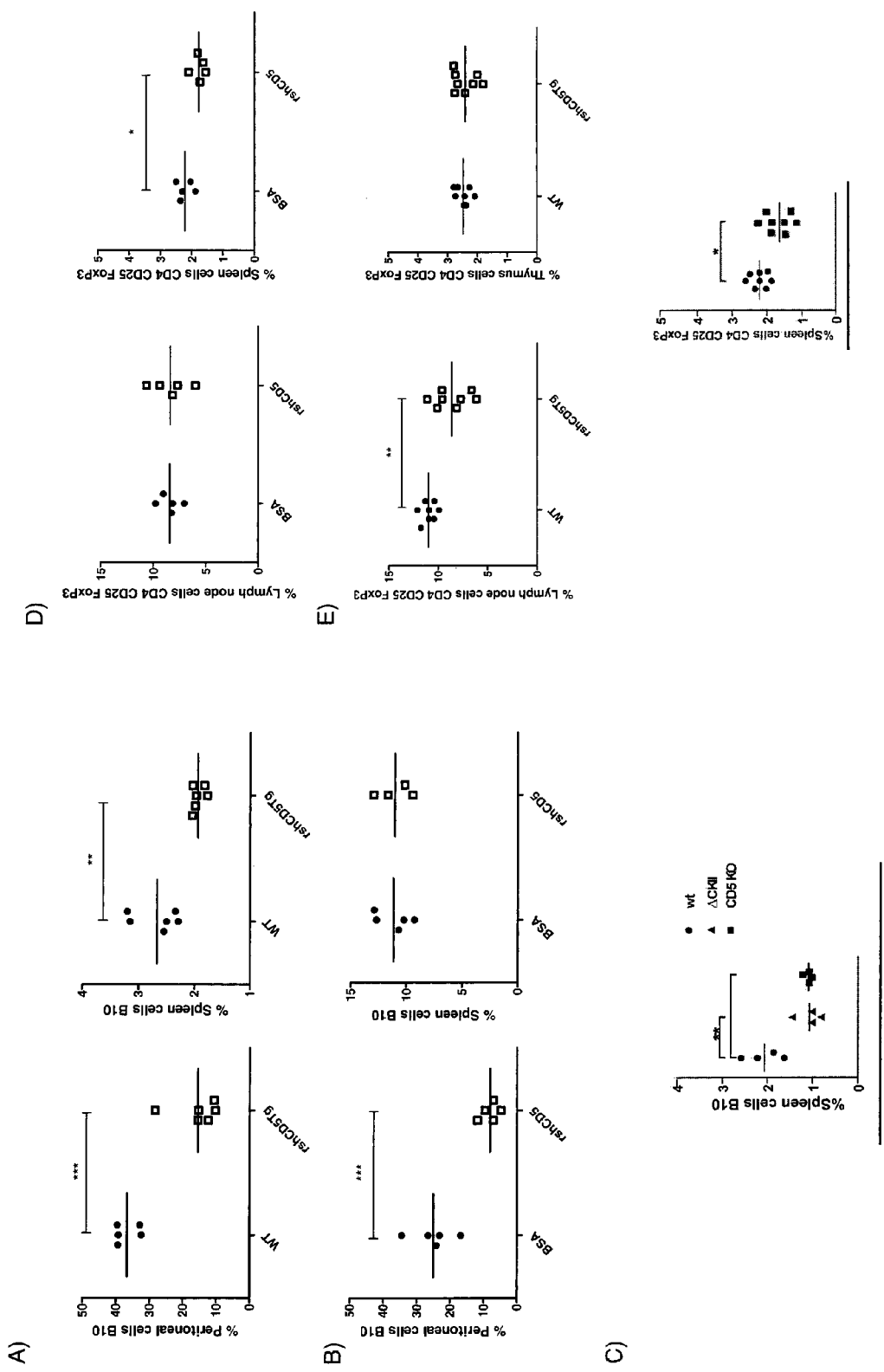
FIG. 6, also relating to Example 2, shows the analysis of regulatory B (Breg) cells and regulatory T (Treg) cells. Panel A shows the analysis of Breg cells (stained with antibodies against B220, IL-10, CD1d, CD5) in peritoneal lavage (PC) and spleen (SC) from rshCD5tg transgenic (square) and non-transgenic mice (wt or circle dots). Panel B shows the change in Breg subpopulations caused by exogenous administration of rshCD5 (shrCD5) to non-transgenic wild-type C57Bl/6 mice. Panel C shows the percentage of spleen Breg (SC B10) cells in mice deficient for CD5 (CD5 KO) and transgenic mice expressing a truncated form of CD5 (ΔCKII). Panel D shows the change in Treg subpopulations (stained with anti-CD4, anti-CD25 and anti-FoxP3) caused by exogenous administration of rshCD5 (shrCD5) to non-transgenic wild-type C57Bl/6 mice. Finally, panel E shows the analysis of Treg cells (stained with mAbs against CD4, CD25 and FoxP3) in thymus (TC), spleen (SC) and lymph node (LNC) from rshCD5tg and non-transgenic mice.

The inventors further analyzed the presence of the regulatory B10 (B220+CD1d+CD5+IL10+) cell subpopulation in samples from peritoneal lavage and spleen of transgenic rshCD5Tg mice and non-transgenic littermates (wt). As can be seen from FIG. 6, panel A, B10 cells were significantly decreased in both peritoneal lavage (PC) and spleen (SC) cell samples. Moreover, as depicted in FIG. 6, panel C, spleen B10 cells (SC) were also decreased in CD5 knock-out mice (CD5−/−) and in CD5ΔCKII mouse line, which expresses a truncated form of CD5 that lacks a Casein Kinase II binding/phosphorylation site at the C-terminal end of its cytoplasmic tail, and is thus unable to transduce intracellular signals.

In addition, CD5-mediated signals are thought to regulate the generation of thymus-derived natural T regulatory cells (nTregs). Thus the inventors monitored the proportion of natural T regulatory cells (nTregs) by staining with surface anti-CD4, anti-CD8, anti-CD25 and intracellular Foxp3. According to FIG. 6, panel E, no differences in the percentage or number of nTregs were observed in the thymus (TC) of rshCD5tg mice compared to wild-type littermates. However, a significant reduction in the percentage and total cell numbers of CD4+CD25+Foxp3+ Tregs was observed in the spleen (SC) and inguinal lymph node (LNC) of transgenic rshCD5tg mice as compared to their non-transgenic littermates.

Figure 7:
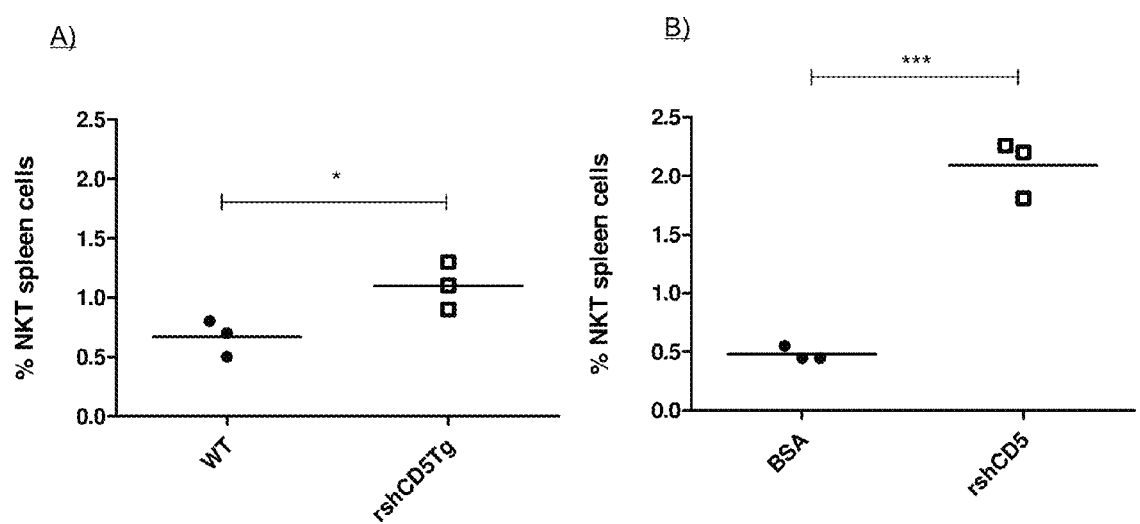
FIG. 7, also relating to Example 2, shows in panel A that rshCD5tg transgenic mice (square dots) show an increased number of NKT cells in the spleen as compared to non-transgenic mice (circle dots). Panel B shows that this increase can also be observed after administration of rshCD5 or a control unrelated protein (Bovine seroalbumin, BSA) to wild-type C57Bl/6 mice. NKT cells were identified by means of staining with mAbs directed against CD3 and NK1.1.

Natural killer T (NKT) cells constitute a subpopulation with anti-infectious and anti-tumoral properties; these cells are characterized by co-expression of the NK1.1 marker and CD3. Total NKT cells were clearly increased in the spleen of transgenic rshCD5 mice, as compared to non-transgenic littermates, as can be seen in FIG. 7, panel A. Interestingly, the infusion of purified exogenous rshCD5 protein (25 μg for two weeks at alternate days) in wild-type non-transgenic C57Bl/6 mice, induced a similar increase in spleen NKT cells as compared to BSA-infused control mice (FIG. 7, panel B).

Overall, these data suggest that transgenic rshCD5tg mice show a significant decrease in the number and/or proportion of some cell subpopulations with known regulatory function (B1a, B10, Treg), as compared to their non-transgenic littermates. This decrease in regulatory cells could have important consequences in the immune response of these mice. Moreover, transgenic rshCD5tg mice also show a significant increase in the number and/or proportion of some cell subpopulations with relevant effector functions (MZ B-cells, NKT cells). Once again, this increase in effector cells could have important consequences in the immune responses of these mice.

It is of note that, since the changes observed on regulatory and/or effector cell subpopulations could be ascribed to a possible deleterious effect of random integration of the transgene copies into the mouse genome, rather than to increased levels of rshCD5, the inventors performed subpopulation analyses in wild-type non-transgenic mice treated with repeated intraperitoneal (i.p.) doses of affinity-purified exogenous rshCD5 (SEQ ID NO: 2). As depicted in FIG. 5 panel B, FIG. 6 panels B and D, and FIG. 7 panel B, all the changes in cell subpopulations reported for transgenic rshCD5tg mice mentioned above were readily reproduced in normal non-transgenic wild-type mice after repeated infusion of purified exogenous rshCD5 protein. These data indicate that increased levels of rshCD5 are responsible for the decrease in specific regulatory subpopulations (B1a, B10, Treg), as well as for the increase in specific effector subpopulations (MZ B-cells, NKT cells).

To further prove the functional relevance of the cell subset changes observed in transgenic rshCD5tg mice, their immune responses were analyzed under several experimental conditions. First, these mice were subjected to two different experimental models of autoimmunity, namely experimental allergic encephalomyelitis (EAE) and collagen-induced arthritis (CIA).

Figure 8:
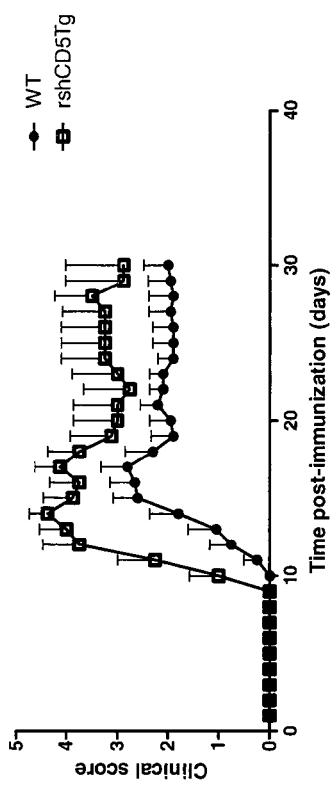
FIG. 8, relating to Example 2, shows the analysis of Experimental Allergic Encephalitis (EAE) induction in rshCD5tg transgenic (square dots) and non-transgenic C57BL/6 mice (circle dots). Disease progression is represented as clinical score (CS) as a function of time (T in days (d)) post-disease induction.

EAE, a well-accepted model resembling human multiple sclerosis, was induced mice by immunization with the myelin oligodendrocyte glycoprotein (MOG) peptide in Complete Freund's Adjuvant (CFA) according to standard protocols. As shown in FIG. 8, the clinical score (CS) of the disease was significantly increased in transgenic rshCD5tg mice as compared to non-transgenic littermates. The data from FIG. 8 were compiled from subcutaneous administration of antigen (MOG) in CFA in 8-10 week old mice. At the time of immunization and 48 h later, 200 ng of Pertussis toxin were also injected intra-peritoneally. Clinical Score (CS) was determined daily and it represents the average values for each mice, where 0=no disease; 0.5=partially motionless tail; 1=motionless tail; 2=ataxia; 3=loss of mobility in one limb; 4=loss of mobility in back limbs; 5=moribund. The graphs show the comparison between CS of transgenic rshCD5tg mice (n=5) (square dots) and non-transgenic mice (C57B16; n=10; round dots).

Figure 9:
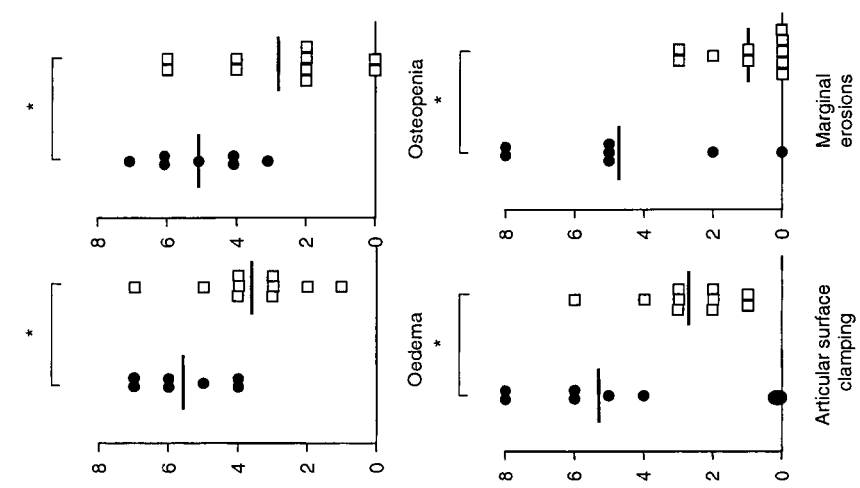
FIG. 9, also relating to Example 2, shows the analysis of the induction of Collagen Induced Arthritis (CIA) in rshCD5tg transgenic (square dots) and non-transgenic mice or wild-type (circle dots). Disease progression is represented as CS. Individual scores for radiological manifestations (joint impingement, JI; marginal erosions, ME; edema, E; and osteopenia, O) are shown for each mice.
Figure 10:
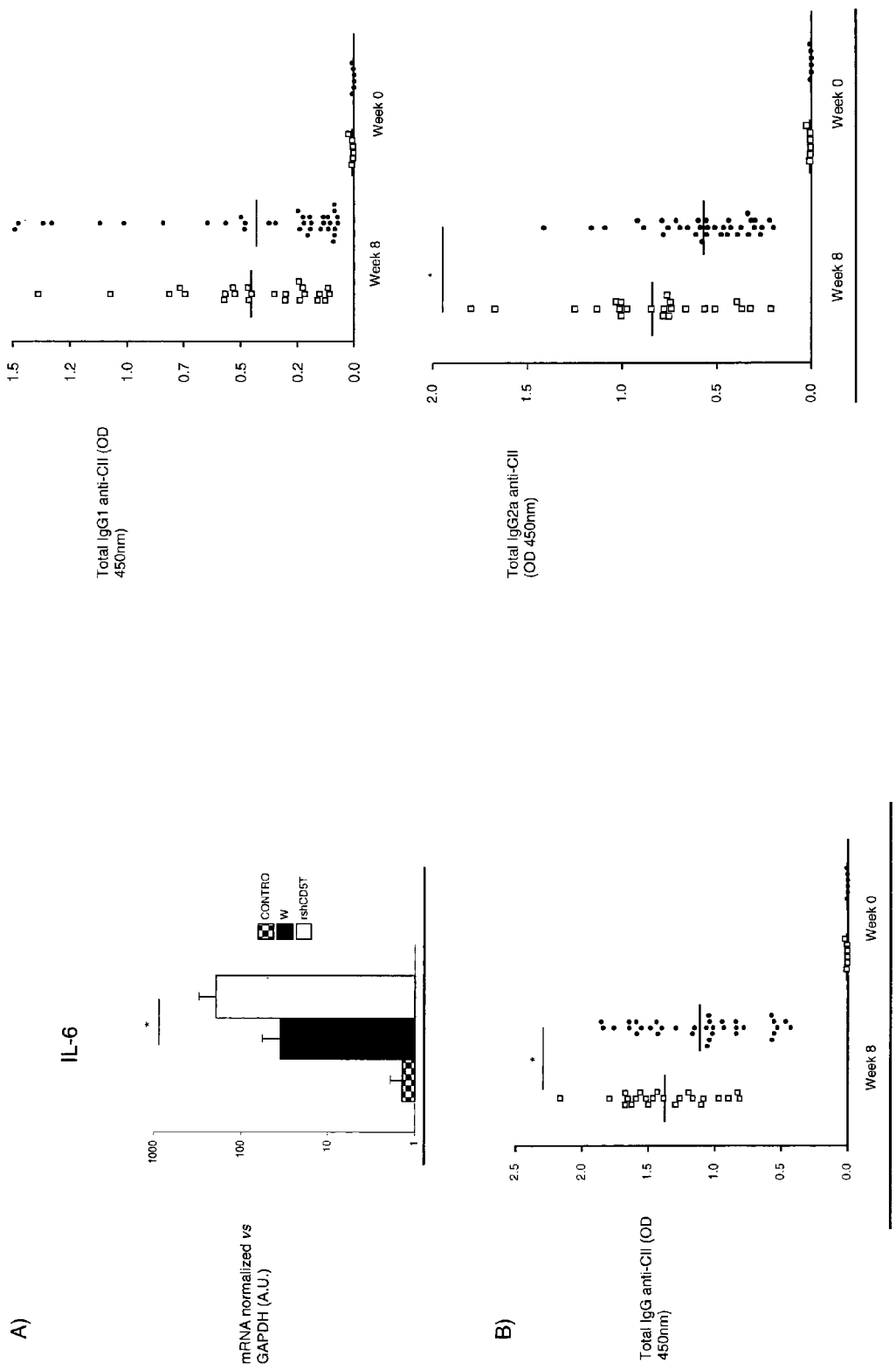
FIG. 10, also related to Example 2, shows cytokine and anti-collagen antibody levels in F1 mice resulting from crossing DBA/1 mice with transgenic rshCD5Tg (F1 TgCD5+) and non-transgenic C57BL/6 mice (F1 WT) following induction of CIA.

Another well-established model of T-cell mediated auto-immune disease is collagen-induced arthritis (CIA) in (B6× DBA/1) F1 mice, which resembles rheumatoid arthritis. As shown in FIG. 9, increased severity of arthritis symptoms (edema (E), articular clamping (JI), marginal erosion (ME), osteopenia (O)), as well as an increase in overall clinical score (CS) were observed in transgenic rshCD5tg mice as compared to non-transgenic littermates. Moreover, IL-6 levels were significantly increased in transgenic rshCD5 mice as compared to non-transgenic mice (FIG. 10, panel A); other pro-inflammatory cytokines also showed slight increases in transgenic mice, although these were not significant as measured by quantitative RT-PCR (data not shown). Antibody levels against type II collagen were also increased in transgenic mice as compared to non-transgenic littermates; these were mostly IgG2 (FIG. 10, panel B), which is indicative of an exacerbated Th1 response.

Altogether, the data obtained with two mouse models of induced autoimmune disease support the notion that transgenic rshCD5tg mice display exacerbated autoimmune responses as compared to non-transgenic littermates. This phenotype of exacerbated induced autoimmunity is compatible with the observed decrease in B and T cell subpopulations with well-known regulatory function, characteristic of these transgenic mice.

Thus, the non-human transgenic mice of the invention represent promising starting points for the study of autoimmune diseases, as well as for the screening of compounds to treat such disorders.

Example 3

Figure 11:
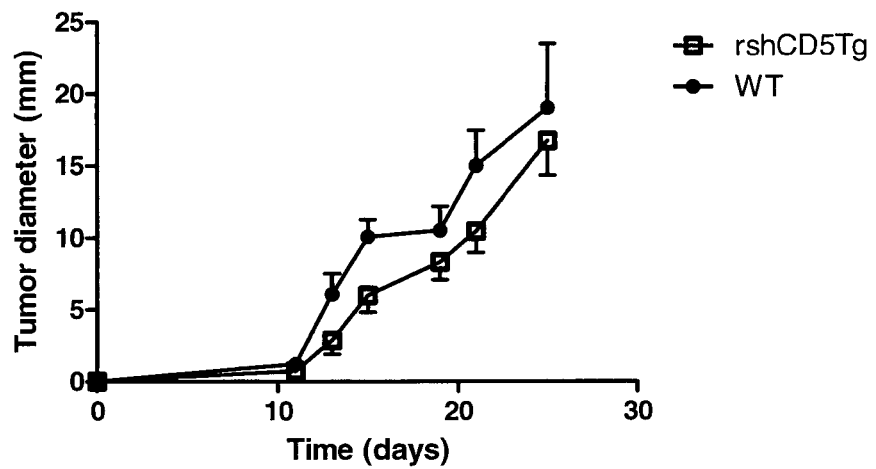
FIG. 11, related to Example 3, is a graph showing B16 melanoma tumour growth in transgenic rshCD5tg mice (squares) in comparison with non-transgenic wild-type (circles) C57Bl/6 mice (wt). TD is the tumour diameter in millimeters (mm); T is time in days (d).

Reduced Growth of B16 Melanoma, RMA-S Lymphoma and MCA205 Sarcoma Tumours in Transgenic rshCD5Tg Mice or in Wild-Type Non-Transgenic C57Bl/6 Mice Treated with Exogenous rshCD5 Plus Chemotherapy To further explore the functional consequences of the decrease in T and B regulatory cell subpopulations as well as the increase in NKT effector cell subpopulations observed in transgenic rshCD5tg mice, the anti-tumoral immune response to B16 mouse melanoma cells was analyzed. B16 cells ($1 \times 10^5$) were injected subcutaneously (s.c.) into either transgenic rshCD5tg mice or their non-transgenic littermates, and tumour growth was recorded over time with a calibre. As shown in FIG. 11, B16 tumours grew significantly more slowly in transgenic rshCD5tg mice as compared to non-transgenic mice.

Figure 12:
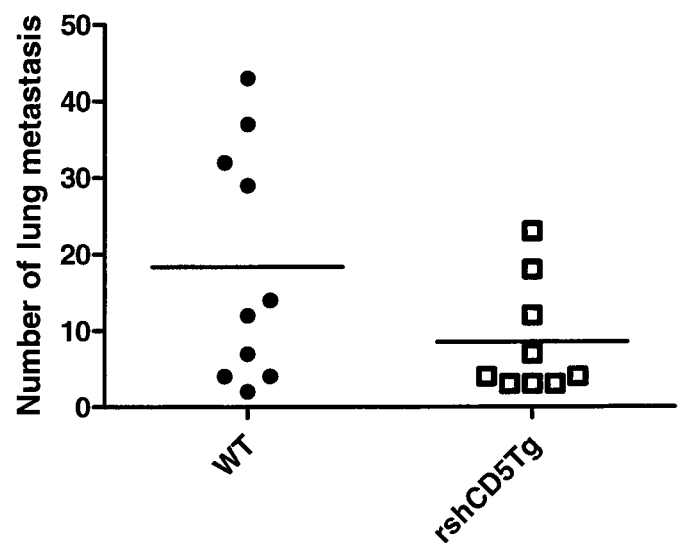
FIG. 12 is the result of an experimental metastasis assay comparing transgenic rshCD5tg mice (square dots) with non-transgenic mice wild-type C57Bl/6 (wt, circle dots). NM means number of macroscopic lung metastases counted on the lung surface 15 days after i.v. injection of B16 cells.

Taking these data into account, the inventors also evaluated a potential improved response of transgenic rshCD5tg mice on metastatic dissemination by intravenously (i.v.) injecting $2 \times 10^5$ B16 melanoma cells. Fifteen days later, mice were sacrificed, their lungs removed and the metastases on the lung surface counted. In FIG. 12 it is depicted the result of this experimental metastasis assay, which revealed a trend ($p=0.099$) towards the decrease in the number of lung metastases observed in rshCD5tg as compared to non-transgenic littermates.

Figure 13:
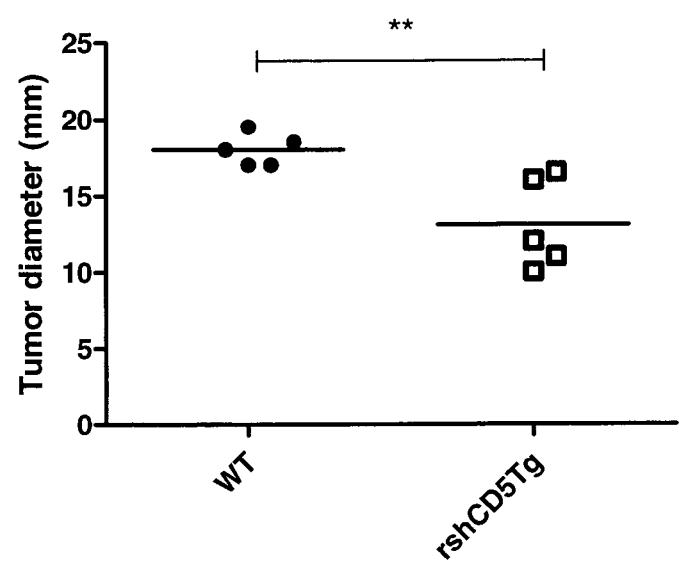
FIG. 13 shows the tumour diameter (TD) in mm observed 18 days after injection of tumour cells in C57Bl/6 mice. Mice were treated with rshCD5 (SEQ ID NO: 2, 25 μg every 48 h from the day of tumour cell injection) plus chemotherapy (a single dose of vincristine 0.5 mg/kg plus doxorubicin 3.3 mg/kg at day 3 post-tumour cell injection) (rshCDD5, square dots) or with chemotherapy alone (vehicle, V, circle dots).

Furthermore, a potential synergic effect of standard chemotherapeutic treatment and rshCD5 was tested. Wild-type C57Bl/6 mice implanted s.c. with $1 \times 10^5$ B16 cells were treated with a single dose of conventional chemotherapy (vincristine 0.5 mg/kg, doxorubicin 3.3 mg/kg) at day 3 after tumour injection; some mice were additionally infused with rshCD5 (25 μg of SEQ ID NO: 2) administered every 48 h from the day of tumour injection. As seen in FIG. 13, tumour progression was slowed down in wild-type non-transgenic mice treated with chemotherapy plus rshCD5 (SEQ ID NO: 2), as compared to same type of mice but treated with chemotherapy plus vehicle (V).

Figure 14:
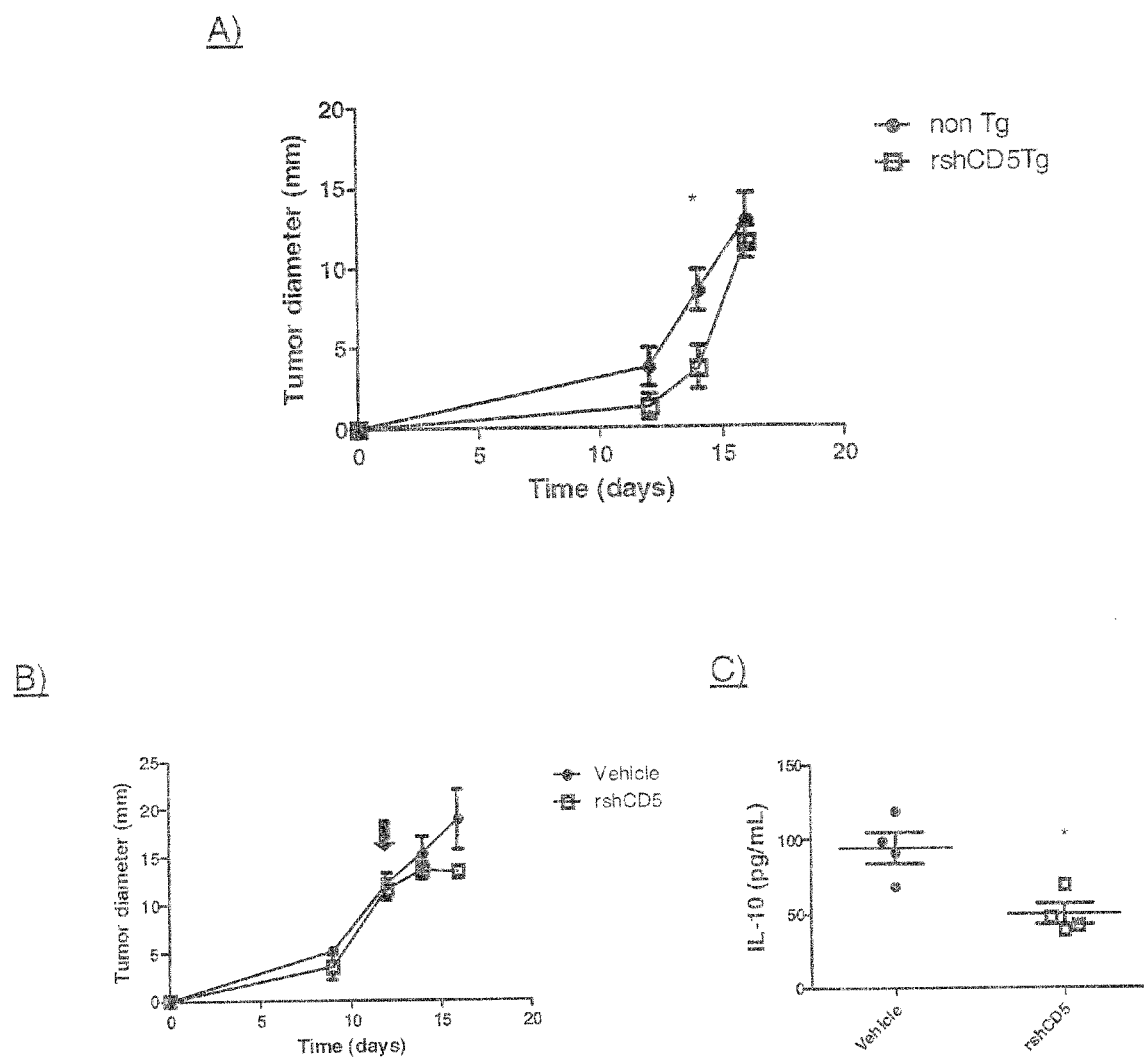
FIG. 14, related to Example 3, shows the growth of RMA-S lymphoma cells in vivo. $5 \times 10^4$ (A) RMA-S cells were injected s.c. in the dorsal area of rshCD5Tg or non-transgenic C57Bl/6 mice (n=5-7 per group). Tumor growth was monitored three times a week with a Vernier calliper. (B) $1 \times 10^5$ RMA-S cells were injected s.c. in the dorsal area of C57Bl/6 mice (n=5 per group). Mice were treated with vehicle or rshCD5 (25 μg) i.p. every 48 hs starting at day 5. Chemotherapy (doxorubicin 2 mM, 50 μl) was administered intratumorally on day 14 (arrow). Tumor growth was monitored three times a week with a Vernier calliper. (C) RMA-S tumors were excised and a tumor lysate obtained by mechanical disruption with a dunce homogeneizer. Intratumoral IL-10 cytokine was then measured in crude tumor lysate by ELISA. Results are expressed per mg of total protein.

In order to show that the effects observed were not dependent on the tumor type, a different tumor cell line was chosen, RMA-S, which is a lymphoma cell line syngeneic with C57Bl/6 mice. RMA-S cells ($2 \times 10^5$ or $5 \times 10^4$, depending on the experiment) were injected s.c. in the dorsal region of rshCD5Tg mice and of non-transgenic littermates, and tumor growth was recorded over time by measuring with a calliper. As shown in FIG. 14A, RMA-S tumours grew significantly more slowly in transgenic rshCD5tg mice as compared to non-transgenic mice. This effect was reduced when higher number of cells were injected (data not shown), indicating that the enhanced immune response has limited ability to control tumor growth when large amounts of tumor cells are injected.

Tumor therapy usually includes simultaneous treatment with more than one drug, and thus it was speculated that rshCD5 might act as an adjuvant to a standard chemotherapy drug. Wild-type C57Bl/6 mice implanted s.c. with $1 \times 10^5$ RMA-S cells were treated with a single dose of conventional chemotherapy (doxorubicin 2 mM, 50 μl) administered intratumorally when tumors reached a diameter >5 mm. Some mice were additionally infused with rshCD5 (25 μg of SEQ ID NO: 2) administered every 48 h from the day of tumour injection. As seen in FIG. 14B, tumour progression was slowed down in wild-type non-transgenic mice treated with chemotherapy plus rshCD5 (SEQ ID NO: 2), as compared to mice treated with chemotherapy plus vehicle. Cytokines were determined in crude tumor lysates by ELISA, and results showed a significant decrease in tumor IL-10 in tumors treated with chemotherapy plus rshCD5 as compared to tumors treated with chemotherapy alone (FIG. 14C); this suggests that the addition of rshCD5 contributes to reduce immunosuppressive conditions within the tumor when treated with chemotherapy, which might help the natural anti-tumor immune response.

Figure 15:
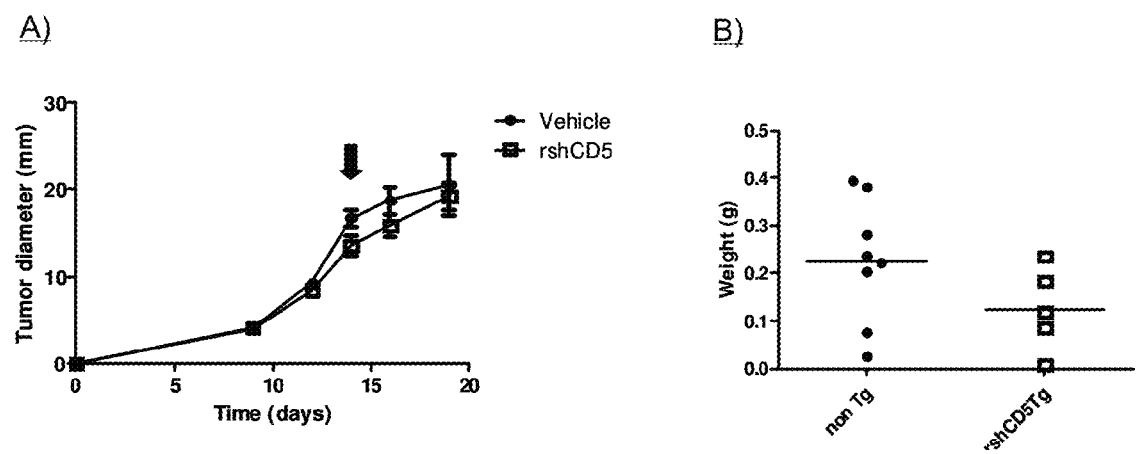
FIG. 15, also related to Example 3, shows the growth of MCA205 sarcoma cells in vivo. (A) $5 \times 10^4$ MCA205 cells were injected s.c. in the dorsal area of rshCD5Tg or non-transgenic C57Bl/6 mice (n=8 for non-Tg and n=6 for rshCD5Tg). Chemotherapy (doxorubicin 2 mM, 50 μl) was administered i.p. on day 14 (arrow). (B) Tumors were excised, measured and weighed at the end of the experiment. Tumor weight in grams.

Lymphoma tumors are considered to be immunogenic, which might favour the immune response against them; poorly immunogenic tumors, such as sarcomas, might not respond well to an immune system-enhancing therapy. The MCA205 tumor, a sarcoma syngeneic with C57Bl/6 mice, was then tested in transgenic versus non-transgenic mice, which were injected s.c. with $2 \times 10^5$ tumor cells. MCA205 cells grew slightly more slowly in rshCD5Tg mice as compared to non-transgenic mice (data not shown). Considering the results obtained with the RMA-S cells, in which the effect of rshCD5 was observed when mice were injected with low cell numbers, the experiment was repeated with a lower amount of cells ($5 \times 10^4$) and both rshCD5Tg and non-transgenic mice were treated with a single dose of chemotherapy (doxorubicin 2 mM, 50 μl, intratumoral) when tumors reached a diameter >5 mm. As shown in FIG. 15A, although tumors appeared to grow only slightly slower in rshCD5Tg as compared to non-transgenic mice, a definite tendency to lower tumor weight was observed in transgenic as compared to non-transgenic mice (FIG. 15B).

Altogether, these data support the notion that transgenic rshCD5tg mice present exacerbated anti-tumoral immune responses compared to their non-transgenic littermates. This phenotype of exacerbated anti-tumoral response is also compatible with the observed decrease in B and T cell subpopulations with well-known regulatory function as well as the increase in effector cell subpopulations with well-known anti-tumoral function, both characteristic of transgenic rshCD5tg mice and of non-transgenic mice infused with repeated doses of purified exogenous rshCD5 protein. These mice represent promising starting points for the study of new anti-tumoral strategies based on the use of rshCD5, either alone or as an adjuvant of current and/or future cancer therapies.

Example 4

Increased Humoral Responses to Immunization with T-Independent Type 1 Antigens

Figure 16:
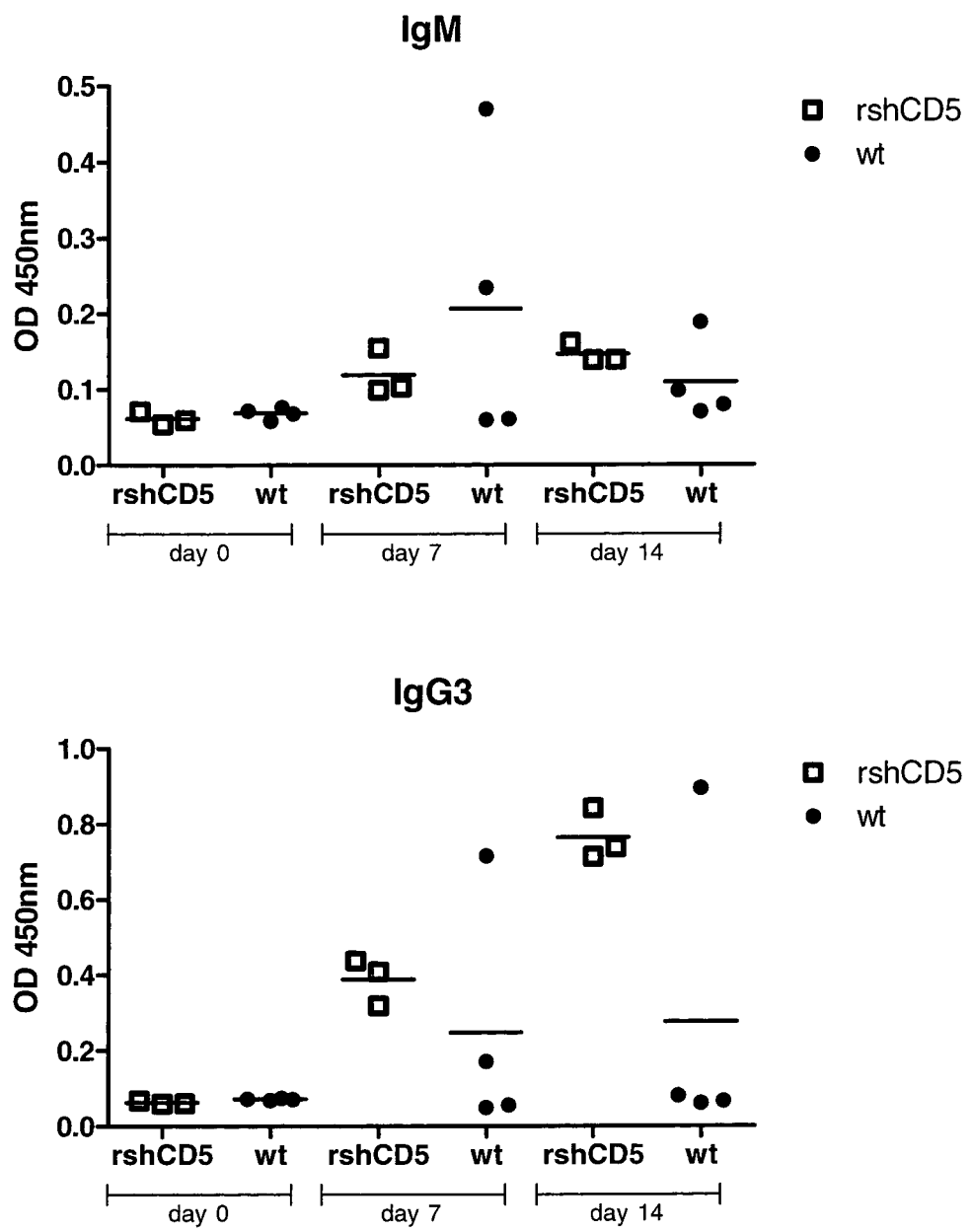
FIG. 16, related to Example 4, shows hapten-specific antibody responses in transgenic rshCD5tg mice. Type I T-independent response in transgenic rshCD5tg mice (n=3, triangle dots) and non-transgenic wild-type C57Bl/6 mice (n=4, square dots) littermates was determined by antibody production following mice immunization. The mice received one i.p. injection of 50 μg of TNP-LPS. TNP-specific IgM and IgG2b, IgG2c, and IgG3 titers were determined at days 0 (d0), 7 (d7), and 14 (d14) by ELISA (OD, optical density, 450 nm) using a 1/2000 dilution of the serum.
Figure 16:
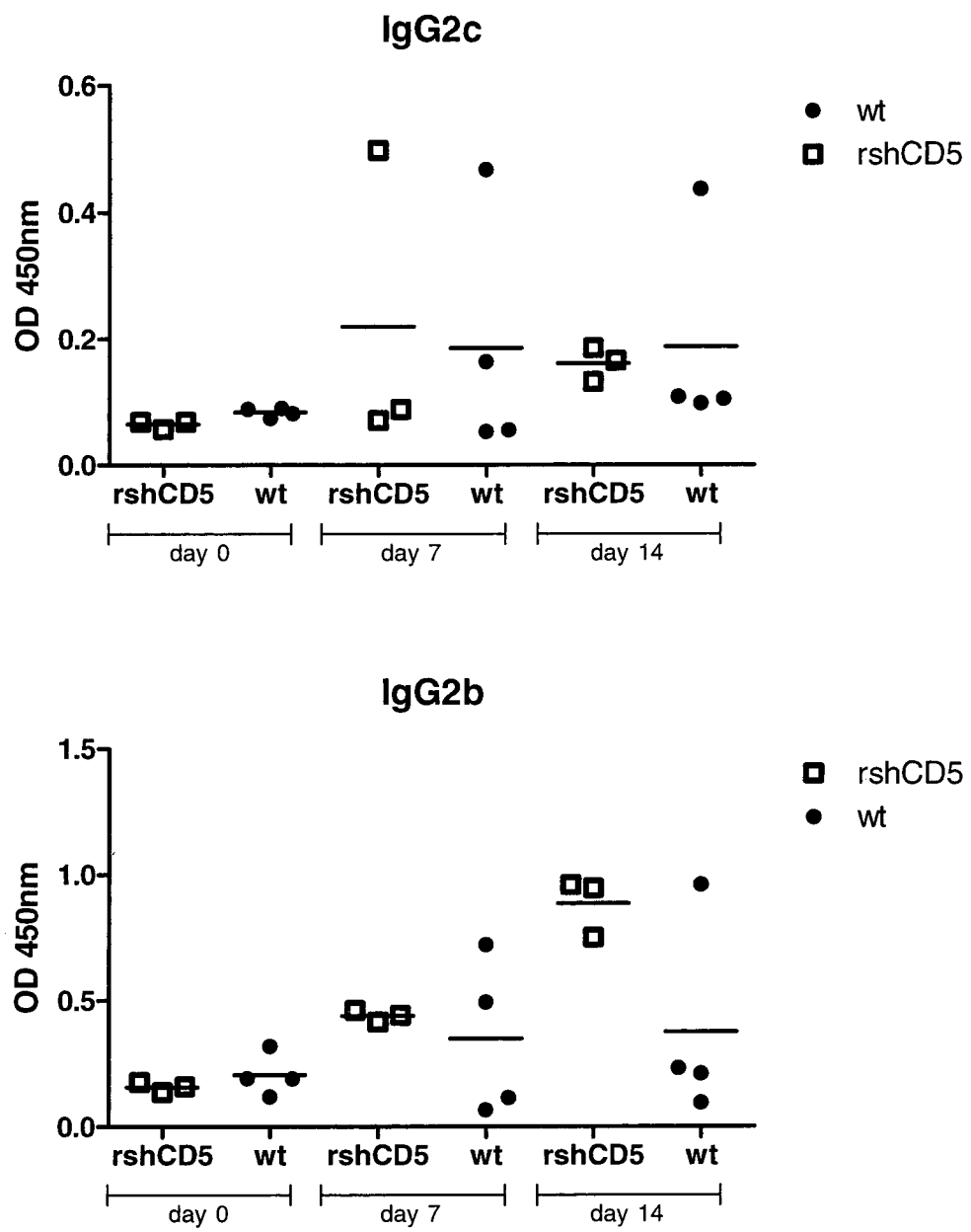

The induction of CIA showed the existence of increased Th1 humoral responses to a T-dependent (TD) antigen (collagen) in transgenic rshCD5tg mice as compared to their non-transgenic littermates. To further investigate the possible existence of increased humoral responses also to T-independent antigens, the inventors immunized transgenic rshCD5tg mice with TNP (trinitrophenyl)-LPS, a well-known T-independent type 1 (TI-1) antigen. The levels of specific antibodies from different immunoglobulin types and subtypes were measured by ELISA in mice serum post-immunization. As shown in FIG. 16, transgenic rshCD5tg mice displayed increased levels of IgG2b and IgG3 antibodies in response to the immunization, as compared to non-transgenic C57Bl/6 mice.

Altogether, these data indicate that transgenic rshCD5tg mice present exacerbated humoral immune responses to both TD and TI-1 antigens as compared to their non-transgenic littermates. This phenotype of exacerbated humoral responses is also compatible with the observed decrease in B and T cell subpopulations with well-known regulatory function as well as the increase of MZ B-cells characteristic of transgenic rshCD5tg mice and of non-transgenic mice infused with repeated doses of purified exogenous rshCD5 protein. This represents promising starting points for the use of rshCD5 as adjuvant for administration together with antigens, particularly together with poorly immunogenic antigens such as TI-1 are.

Example 5

Figure 17:
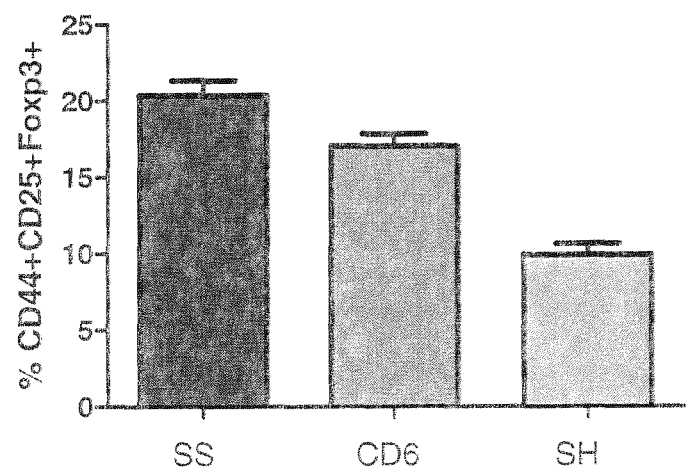
FIG. 17, related to Example 5, is the result of an analysis of spleen Treg subpopulations (% CD44+CD25+Foxp3+) at day 3 post-induction of sepsis. In the chosen model, experimental sepsis was induced by cecal ligation and puncture (CLP) in wild-type C57Bl/6 mice. Regulatory T cell subpopulations were analyzed in sham (SH) operated mice, untreated mice (saline solution, SS) and in mice treated with rshCD6 (CD6). P value between SS and CD6 groups <0.05.

Infusion of Soluble CD6 Significantly Reduces the Increase of Splenic Treg Cells Observed in the Post-Sepsis Period Scavenger-like lymphocyte receptors CD5 and CD6 share a great degree of structural homology, as well as functional similarity and a similar expression pattern. The inventors have shown that both soluble CD5 and CD6 are effective in mouse models of fungal and bacterial sepsis, respectively. Mice surviving sepsis are known to be immunodepressed as deduced from increased numbers of spleen Treg cells. As seen in FIG. 17, a single dose (1 mg/Kg) of recombinant soluble human CD6 (rshCD6 or SEQ ID NO: 3) significantly reduces the numbers of spleen Treg cells observed 3 days post-induction of a polymicrobial sepsis (by cecal ligation and puncture) in wild-type C56Bl/6 mice compared to untreated mice (p<0.05). This supports the notion that soluble CD6 also possesses immunomodulatory properties by influencing the dynamics of cell subpopulations with regulatory function, as previously depicted for rshCD5 (SEQ ID NO: 2) in Example 2. These immunomodulatory properties of rshCD6 might be of use in the prophylaxis or therapy of cell growth disorders, in a similar way to that of rshCD5.

The soluble ectodomain of human CD6 (rshCD6, SEQ ID NO: 3) was expressed in HEK 293-EBNA by using an episomal expression system as reported by Gimferrer I et al. "Relevance of CD6-mediated interactions in T cell activation and proliferation" *J Immunol.* 2004, Vol. 173, pp.: 2262-2270. Briefly, the extracellular region of CD6 was amplified by PCR using SEQ ID NO: 11 (5'-CTTCTAGATGACCAGCTCAACACCACCAGCA-3') and SEQ ID NO: 12 (5'-GCGGATCCCTATTCTATAGTGACTGTCTGAACA-3') as forward and reverse primers, respectively, and the CD6-PB1 cDNA as a template. The PCR product was XbaI/BamHI restricted and cloned into the appropriately digested pCEP-Pu vector. The resulting construct was transfected into HEK 293-EBNA cells, as described. The rshCD6 protein was affinity purified over CNBr-activated Sepharose 4B columns covalently coupled to 168.1 (anti-human CD6) mouse mAb.

Example 6

Reduced Growth of B16 Melanoma and RMA-S Lymphoma Tumours in Transgenic rshCD6Ick Mice (Example 7) or in Wild-Type Non-Transgenic C57Bl/6 Mice Treated with Exogenous rshCD6 Plus Chemotherapy The melanoma cell line B16, syngeneic with the C57Bl/6 mouse strain, was used for these experiments. rshCD6Ick mice were injected with $1 \times 10^5$ B16 cells and tumor growth measured over time. As shown in FIG. 18A, rshCD6Ick mice displayed a slightly slower tumor growth rate mainly at early time points as compared to non-transgenic mice.

To investigate a possible synergistic effect of rshCD6 and chemotherapy, $1 \times 10^5$ B16 cells were injected s.c. in wild-type C57Bl/6 mice, which were treated with a single dose of chemotherapy (vincristine 0.5 mg/kg, doxorubicin 3.3 mg/kg, i.p.) at day 3 after tumour injection; mice were additionally infused with vehicle or rshCD6 (25 µg) administered every 48 h from the day of tumour injection. As seen in FIG. 18B, tumour progression was slowed down at early time points in wild-type non-transgenic mice treated with chemotherapy plus rshCD6, as compared to mice treated with chemotherapy plus vehicle.

A similar experiment was carried out with RMA-S lymphoma cells. $1 \times 10^5$ RMA-S cells were injected s.c. in wild-type C57Bl/6 mice, which were treated with doxorubicin 3.3 mg/kg, i.p., at days 5 and 12 after tumour injection; mice were additionally infused with vehicle or rshCD6 (25 µg) administered every 48 h from the day of tumour injection. As seen in FIG. 18C, tumour progression was significantly slowed down in wild-type non-transgenic mice treated with chemotherapy plus rshCD6, as compared to mice treated with chemotherapy plus vehicle.

Example 7

Generation of rshCD6Ick Transgenic Mice (Mice Over-Expressing SEQ ID NO: 3 or Human Soluble CD6 Isoform)

Figure 20:
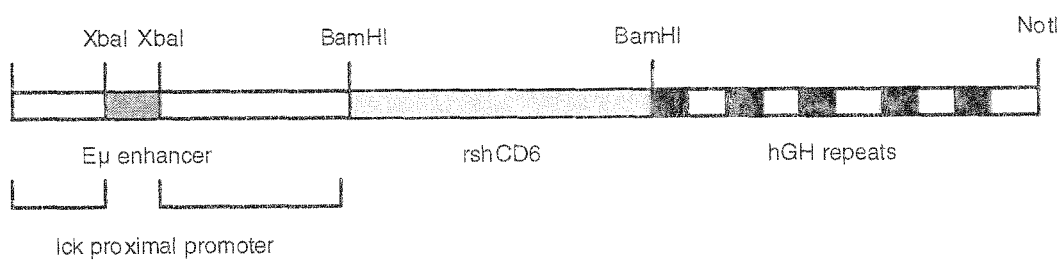
FIG. 20 is a schematic drawing of the expression vector construction for expressing human recombinant soluble protein CD6 (rshCD6 or SEQ ID NO: 3). rshCD6 means SEQ ID NO: 3; XbaI, NotI, BamHI are the sites of restriction endonucleases; Ick proximal promoter is the sequence encoding the proximal promoter of the Ick kinase; Eμ is the sequence encoding the Eμ enhancer; p1026xrshCD6 is the expression vector to produce rshCD6 or SEQ ID NO: 3.

In an attempt to investigate the functional relevance of shCD6 in vivo, the inventors generated a new strain of mice which expresses recombinant shCD6 (rshCD6, also named SEQ ID NO: 3) under the control of the Ick promoter and the Eµ enhancer (FIG. 20). This approach is intended to drive the expression of rshCD6 preferentially in T and B lymphocytes. The Ick promoter is disclosed in Garvin et al "Structure of the murine Ick gene and its rearrangement in a murine lymphoma cell line". Mol Cell Biol 1988 Vol. 8(8), pp.: 3058-64.

The sequence coding for rshCD6 (SEQ ID NO: 3) was cloned into the p1026x vector. This vector was created by ligating a 0.92 bp fragment of the immunoglobulin heavy chain enhancer (Eµ) into the XbaI site within the Ick proximal promoter portion of the p1017 vector (Chaffin et al. "Dissection of thymocyte signaling pathways by in vivo expression of pertussis toxin ADP-ribosyltransferase" *EMBO J*—1990 Vol. 9, pp: 3821-3829). Surprisingly, transgenic mice that were initially created using this construct produced both functional human growth hormone as well as products encoded by the H-rasN17 cDNA (data not shown), possibly due to re-initiation of translation. Therefore, the BglII site in the fourth exon of hGH was cleaved, filled in and religated, resulting in the generation of an in-frame stop codon. This treatment, yielding the mutant hGx cassette, has been shown to prevent expression of functional growth hormone protein in similar transgenic constructs (Iritani et al. "Control of B cell development by Ras-mediated activation of Raf" *EMBO J*—1997 Vol. 16(23), pp: 7019-7031).

The fragment containing the rshCD6 sequence (SEQ ID NO: 3) was synthesized at GenScript facilities (New Jersey, USA) into the pUC57 vector, cut with BamHI and cloned into the BamHI site of the p1026x vector, with an orientation such that the 5' end was located directly downstream of the lck proximal promoter and the 3' end was located upstream of the hGH repeats.

Transgenic mice were generated at PolyGene facilities (Rümlang, Switzerland). The lck-CD6 fragment of the expression plasmid was excised from the p1026x vector (together with the Eμ enhancer, lck promoter and hGH repeats) with NotI restriction endonucleases by cleaving 10 μg of the plasmid. The fragment was purified from SeaKem GTG agarose (avoiding exposure to UV light) using the Qbiogene Geneclean Spin kit, then dialysed 24 h against 2 l microinjection buffer (10 mM Tris.HCl pH 7.2, 0.1 mM EDTA), and diluted to a concentration of 4 ng/μl. The DNA was injected in three sessions into C57BL/6N-derived zygotes. For this purpose, C57BL/6N female mice (bred at PolyGene form parents obtained from Charles River WIGA Sulzfeld) were superovulated at 28-34 days of age and mated in the PolyGene mouse facility to C57BL/6N breeder males, originally also obtained from Charles River.

Injected zygotes were cultivated overnight and transferred into pseudopregnant B6CBAF1 females, also from Charles River. The animals were kept in individually ventilated cages (IVC). The first pups born were biopsied at weaning and analysed for transgene integration by PCR, using the PCR primers SEQ ID NO: 13 (5'-ACCTGACCAGCT-CAACAC-3') and SEQ ID NO: 14 (5'-CAGTAGCGTGT-GACTAGG-3'). Two positive offspring were detected and these were rebiopsied, retested and found positive again.

The obtention of the non-human mice of the invention is thus performed by a) obtaining the construction comprising SEQ ID NO: 3; b) microinjecting the construction of step a) in the pronucleus of a fertilized ovule; c) culturing the fertilized ovule; d) transplanting the ovule to a pseudopregnant mouse female; and e) selecting from the progeny those animals containing cDNA encoding SEQ ID NO: 3 or (rshCD6).

Figure 21:
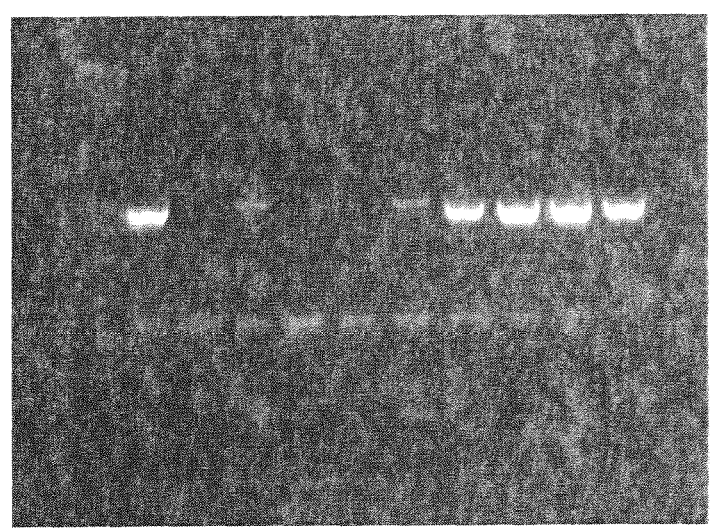
FIG. 21 relating to Example 7, is an image of the agarose gel with the result of PCR amplifications of the nucleotide sequence encoding rshCD6 (SEQ ID NO: 3) from ear DNA. A PCR product encompassing part of the extracellular domains of human CD6 was detected at the expected size (495 base pairs, bp) in the transgenic mice. A fragment of 150 bp corresponding to an exonic region of mouse MHC class II-associated invariant chain (LIEX) gene was also amplified as an internal control for the PCR.

To identify the transgenic mice, a PCR from tail or ear DNA was performed using the forward primer (5'-GCT-GTCCAGTGCCACGAACT-3'), and reverse primer (5'-GAAGCTCCTCTGTGTCCTCAT-3'), which are specific for the extracellular region of human CD6. FIG. 21 shows a representative PCR analysis showing the expected 495 bp band which identifies the transgenic DNA; the 150 bp band corresponds to an internal PCR amplification control from the house-keeping LIEX gene by using the forward primer of SEQ ID NO: 8 (5'-TCACTCAAGGCAACCTT CCTGC-3'), and reverse primer of SEQ ID NO: 9 (5'-CGACCT-CATCTCTAACCATGAACAG-3'). In this experiment, mice 2, 4 and 5 are non-transgenic littermates, while the rest of the mice are positive for the rshCD6 transgene.

REFERENCES CITED IN THE APPLICATION

Hollander et al., "Immunotherapy of lymphoid and nonlymphoid tumours with monoclonal anti-Lyt-1 antibodies", *The Journal of Immunology*—1984, Vol. 133(5), pp.: 2801-2805.

Axtell et al., "Cutting Edge: Critical Role for CD5 in Experimental Autoimmune Encephalomyelitis: Inhibition of Engagement Reverses Disease in Mice", *The Journal of Immunology*—2004, Vol. 173, pp.: 2928-2932.

Brown et al., "A Ligand for CD5 Is CD5", *The Journal of Immunology*—2010, Vol. 185, pp.: 6068-6074.

Calvo et al. "Identification of a natural soluble form of human CD5" Tissue Antigens-1999, Vol. 54(2), pp: 128-37

Ramos-Casals et al "High circulating levels of soluble scavenger receptors (sCD5 and sCD6) in patients with primary Sjögren's syndrome" *Rheumatology*—2001 Vol. 40(9), pp: 1056-1059

Chaffin et al. "Dissection of thymocyte signaling pathways by in vivo expression of pertussis toxin ADP-ribosyltransferase" *EMBO J*—1990 Vol. 9, pp: 3821-3829

Iritani et al. "Control of B cell development by Ras-mediated activation of Raf" *EMBO J*—1997 Vol. 16(23), pp: 7019-7031

Cariappa et al "The recirculating B cell pool contains two functionally distinct, long-lived, posttransitional, follicular B cell populations", *Journal of Immunology*—2007, Vol. 179(4), pp.: 2270-2281

Alberola-Ila et al. "Intracellular events involved in CD5-induced human T cell activation and proliferation" *The Journal of Immunology*—1992, Vol. 148(5), pp: 1287-1293.

Calvo et al. "Interaction of recombinant and natural soluble CD5 forms with alternative cell surface ligand", *Eur. J. Immunol.*—1999, Vol. 29, pp.: 2119-2129.

Jones et al., "Isolation of complementary DNA clones encoding the human lymphocyte glycoprotein T1/Leu-1", *Nature*—1986, Vol. 323, pp.: 346-349.

Gunning et al., "A human β-actin expression vector system directs high-level accumulation of antisense transcripts", *Proc. natl. Acad. Sci. USA.*—1987, Vol. 84, pp.: 4831-4835.

Gimferrer I et al. "Relevance of CD6-mediated interactions in T cell activation and proliferation", *J Immunol.*—2004, Vol. 173, pp.: 2262-2270.

Garvin et al "Structure of the murine lck gene and its rearrangement in a murine lymphoma cell line". Mol Cell Biol 1988 Vol. 8(8), pp.: 3058-64.

The invention claimed is:

1. A method for treating cancer or tumor by enhancing immune response in a subject in need thereof, the method comprising administering to said subject an effective amount of a soluble protein isoform of CD5 or CD6; wherein the soluble protein isoform of CD5 or CD6 comprises a polypeptide sequence selected from the following (a) and (b):
   (a) a polypeptide sequence having 95% or greater sequence identity with SEQ ID NO: 2; or
   (b) a polypeptide sequence having 95% or greater sequence identity with SEQ ID NO: 3, thereby treating said cancer or tumor by enhancing immune response.

2. The method according to claim 1, wherein the CD5 is a human CD5 and the CD6 is a human CD6.

3. The method according to claim 2, wherein the soluble protein isoform comprises a sequence selected from the group consisting of SEQ ID NO: 2 and SEQ ID NO: 3.

4. The method according to claim 1, wherein the tumor is of hematopoietic origin.

5. The method according to claim 1, wherein the cancer is selected from the group consisting of melanoma, sarcoma, colon cancer, skin cancer, epithelioma, colorectal cancer, breast cancer, gastric cancer, ovarian cancer, pancreatic cancer, brain cancer, head and neck cancer, esophageal cancer, testicular cancer, teratoma and cervical cancer.

6. The method according to claim 1, wherein the soluble protein isoform is administered as an adjuvant.

7. The method according to claim 6, wherein the adjuvant is administered together with a T-dependent (TD) antigen.

8. A method for treating cancer or tumor by enhancing immune response in a subject in need thereof, the method comprising administering to said subject an effective amount of a pharmaceutical composition which comprises at least one soluble protein isoform of CD5 or CD6 and a pharmaceutically acceptable excipient or carrier; wherein the soluble protein isoform of CD5 or CD6 comprises a polypeptide sequence selected from the following (a) and (b):
   (a) a polypeptide sequence having 95% or greater sequence identity with SEQ ID NO: 2; or
   (b) a polypeptide sequence having 95% or greater sequence identity with SEQ ID NO: 3, thereby treating said cancer or tumor by enhancing immune response in said subject.

9. The method according to claim 8, wherein the pharmaceutical composition comprises at least one further active ingredient.

10. The method according to claim 9, wherein the further active ingredient is selected from the group consisting of a chemotherapeutic agent and a therapeutic antibody.

11. The method according to claim 9, wherein the further active ingredient is an antigen.

12. A method for enhancing immune response to an immunizing agent in a subject in need thereof, the method comprising administering to said subject an effective amount of a soluble protein isoform of CD5 or CD6; wherein the soluble protein isoform of CD5 or CD6 comprises a polypeptide sequence selected from the following (a) and (b):
   (a) a polypeptide sequence having 95% or greater sequence identity with SEQ ID NO: 2; or
   (b) a polypeptide sequence having 95% or greater sequence identity with SEQ ID NO: 3, thereby enhancing immune response to an immunizing agent in said subject.

13. A method for enhancing immune response to an immunizing agent in a subject in need thereof, the method comprising administering to said subject an effective amount of a pharmaceutical composition which comprises at least one soluble protein isoform of CD5 or CD6 and a pharmaceutically acceptable excipient or carrier; wherein the soluble protein isoform of CD5 or CD6 comprises a polypeptide sequence selected from the following (a) and (b):
   (a) a polypeptide sequence having 95% or greater sequence identity with SEQ ID NO: 2; or
   (b) a polypeptide sequence having 95% or greater sequence identity with SEQ ID NO: 3, thereby enhancing immune response to an immunizing agent in said subject.

14. The method according to claim 1, wherein the tumor is of non-hematopoietic origin.

15. The method according to claim 6, wherein the adjuvant is administered together with a T-independent (TI) antigen.

16. The method according to claim 15, wherein the T-independent (TI) antigen is selected from the group consisting of bacterial capsular polysaccharides of *Streptococcus pneumoniae*, (polymerized) *Salmonella* flagellin, poly-D-amino acids and the *E. coli* lipopolysaccharide.

17. The method according to claim 10, wherein the chemotherapeutic agent is a cytostatic or a cytotoxic agent.

18. The method according to claim 17, wherein the chemotherapeutic agent is selected from the group consisting of vincristine, doxorubicin, carboplatin, cisplatin, paclitaxel, vinorelbine, gemcitabine, irinotecan, docetaxel, dacarbazine, gefinitib, dasatinib, imatinib, etoposide, cyclophosphamide, and mitoxantrone.

\* \* \* \* \*

SEQUENCE LISTING

<160> NUMBER OF SEQ ID NOS: 14

<210> SEQ ID NO 1
<211> LENGTH: 1573
<212> TYPE: DNA
<213> ORGANISM: Homo sapiens

<400> SEQUENCE: 1

```
gagatacccg gccagacacc ctcacctgcg gtgcccagct gcccaggctg aggcaagaga    60
aggccagaaa ccatgcccat ggggtctctg caaccgctgg ccaccttgta cctgctgggg   120
atgctggtcg cttcctgcct cggacggctc agctggtatg acccagattt ccaggcaagg   180
ctcacccgtt ccaactcgaa gtgccagggc agctggagg tctacctcaa ggacggatgg    240
cacatggttt gcagccagag ctggggccgg agctccaagc agtgggagga ccccagtcaa   300
gcgtcaaaag tctgccagcg gctgaactgt ggggtgccct taagccttgg ccccttcctt   360
gtcacctaca cacctcagag ctcaatcatc tgctacggac aactgggctc cttctccaac   420
tgcagccaca gcagaaatga catgtgtcac tctctgggcc tgacctgctt agaaccccag   480
aagacaacac ctccaacgac aaggcccccg cccaccacaa ctccagagcc acagctcct    540
cccaggctgc agctggtggc acagtctggc ggccagcact gtgccggcgt ggtgagttc    600
tacagcggca gcctgggggg taccatcagc tatgaggccc aggacaagac ccaggacctg   660
gagaacttcc tctgcaacaa cctccagtgt ggctccttct tgaagcatct gccagagact   720
gaggcaggca gagcccaaga cccaggggag ccacgggaac accagcccct tgccaatcca   780
tggaagatcc agaactcaag ctgtacctcc ctggagcatt gcttcaggaa aatcaagccc   840
cagaaaagtg gccgagttct tgccctcctt tgctcaggtt ccagcccaa ggtgcagagc    900
cgtctggtgg ggggcagcag catctgtgaa ggcaccgtgg aggtgcgcca gggggctcag   960
tgggcagccc tgtgtgacag ctcttcagcc aggagctcgc tgcggtggga ggaggtgtgc  1020
cgggagcagc agtgtggcag cgtcaactcc tatcgagtgc tggacgctgg tgacccaaca  1080
tcccgggggc tcttctgtcc ccatcagaag ctgtcccagt gccacgaact tgggagaga   1140
aattcctact gcaagaaggt gtttgtcaca tgccaggatt aaaacccgc aggcctggcc   1200
gcaggcacgg tggcaagcat catcctggcc ctggtgctcc tggtggtgct gctggtcgtg  1260
tgcggccccc ttgcctacaa gaagctagtg aagaaattcc gccagaagaa gcagcgccag  1320
tggattggcc caacgggaat gaaccaaaac atgtctttcc atcgcaacca cacggcaacc  1380
gtccgatccc atgctgagaa ccccacagcc tcccacgtgg ataacgaata cagccaacct  1440
cccaggaact cccgcctgtc agcttatcca gctctggaag gggttctgca tcgctcctcc  1500
atgcagcctg acaactcctc cgacagtgac tatgatctgc atggggctca gaggctgtaa  1560
agaactggga tcc                                                     1573
```

<210> SEQ ID NO 2
<211> LENGTH: 345
<212> TYPE: PRT
<213> ORGANISM: Homo sapiens

<400> SEQUENCE: 2

Arg Leu Ser Trp Tyr Asp Pro Asp Phe Gln Ala Arg Leu Thr Arg Ser
1               5                   10                  15

Asn Ser Lys Cys Gln Gly Gln Leu Glu Val Tyr Leu Lys Asp Gly Trp
            20                  25                  30

His Met Val Cys Ser Gln Ser Trp Gly Arg Ser Ser Lys Gln Trp Glu
        35                  40                  45

Asp Pro Ser Gln Ala Ser Lys Val Cys Gln Arg Leu Asn Cys Gly Val
    50                  55                  60

Pro Leu Ser Leu Gly Pro Phe Leu Val Thr Tyr Thr Pro Gln Ser Ser
65                  70                  75                  80

Ile Ile Cys Tyr Gly Gln Leu Gly Ser Phe Ser Asn Cys Ser His Ser

```
                85                  90                  95
Arg Asn Asp Met Cys His Ser Leu Gly Leu Thr Cys Leu Glu Pro Gln
            100                 105                 110

Lys Thr Thr Pro Pro Thr Thr Arg Pro Pro Thr Thr Thr Pro Glu
            115                 120                 125

Pro Thr Ala Pro Pro Arg Leu Gln Leu Val Ala Gln Ser Gly Gly Gln
            130                 135                 140

His Cys Ala Gly Val Val Glu Phe Tyr Ser Gly Ser Leu Gly Gly Thr
145                 150                 155                 160

Ile Ser Tyr Glu Ala Gln Asp Lys Thr Gln Asp Leu Glu Asn Phe Leu
            165                 170                 175

Cys Asn Asn Leu Gln Cys Gly Ser Phe Leu Lys His Leu Pro Glu Thr
            180                 185                 190

Glu Ala Gly Arg Ala Gln Asp Pro Gly Glu Pro Arg Glu His Gln Pro
            195                 200                 205

Leu Pro Ile Gln Trp Lys Ile Gln Asn Ser Ser Cys Thr Ser Leu Glu
            210                 215                 220

His Cys Phe Arg Lys Ile Lys Pro Gln Lys Ser Gly Arg Val Leu Ala
225                 230                 235                 240

Leu Leu Cys Ser Gly Phe Gln Pro Lys Val Gln Ser Arg Leu Val Gly
            245                 250                 255

Gly Ser Ser Ile Cys Glu Gly Thr Val Glu Val Arg Gln Gly Ala Gln
            260                 265                 270

Trp Ala Ala Leu Cys Asp Ser Ser Ala Arg Ser Ser Leu Arg Trp
            275                 280                 285

Glu Glu Val Cys Arg Glu Gln Gln Cys Gly Ser Val Asn Ser Tyr Arg
            290                 295                 300

Val Leu Asp Ala Gly Asp Pro Thr Ser Arg Gly Leu Phe Cys Pro His
305                 310                 315                 320

Gln Lys Leu Ser Gln Cys His Glu Leu Trp Glu Arg Asn Ser Tyr Cys
            325                 330                 335

Lys Lys Val Phe Val Thr Cys Gln Asp
            340                 345

<210> SEQ ID NO 3
<211> LENGTH: 373
<212> TYPE: PRT
<213> ORGANISM: Homo sapiens

<400> SEQUENCE: 3

Asp Gln Leu Asn Thr Ser Ser Ala Glu Ser Glu Leu Trp Glu Pro Gly
1               5                   10                  15

Glu Arg Leu Pro Val Arg Leu Thr Asn Gly Ser Ser Ser Cys Ser Gly
            20                  25                  30

Thr Val Glu Val Arg Leu Glu Ala Ser Trp Glu Pro Ala Cys Gly Ala
            35                  40                  45

Leu Trp Asp Ser Arg Ala Ala Glu Ala Val Cys Arg Ala Leu Gly Cys
            50                  55                  60

Gly Gly Ala Glu Ala Ala Ser Gln Leu Ala Pro Pro Thr Pro Glu Leu
65                  70                  75                  80

Pro Pro Pro Pro Ala Ala Gly Asn Thr Ser Val Ala Ala Asn Ala Thr
            85                  90                  95

Leu Ala Gly Ala Pro Ala Leu Leu Cys Ser Gly Ala Glu Trp Arg Leu
            100                 105                 110
```

```
Cys Glu Val Val Glu His Ala Cys Arg Ser Asp Gly Arg Ala Arg
            115                 120                 125

Val Thr Cys Ala Glu Asn Arg Ala Leu Arg Leu Val Asp Gly Gly
        130                 135                 140

Ala Cys Ala Gly Arg Val Glu Met Leu Glu His Gly Glu Trp Gly Ser
145                 150                 155                 160

Val Cys Asp Asp Thr Trp Asp Leu Glu Asp Ala His Val Val Cys Arg
                165                 170                 175

Gln Leu Gly Cys Gly Trp Ala Val Gln Ala Leu Pro Gly Leu His Phe
            180                 185                 190

Thr Pro Gly Arg Gly Pro Ile His Arg Asp Gln Val Asn Cys Ser Gly
        195                 200                 205

Ala Glu Ala Tyr Leu Trp Asp Cys Pro Gly Leu Pro Gly Gln His Tyr
    210                 215                 220

Cys Gly His Lys Glu Asp Ala Gly Val Val Cys Ser Glu His Gln Ser
225                 230                 235                 240

Trp Arg Leu Thr Gly Gly Ala Asp Arg Cys Glu Gly Gln Val Glu Val
                245                 250                 255

His Phe Arg Gly Val Trp Asn Thr Val Cys Asp Ser Glu Trp Tyr Pro
            260                 265                 270

Ser Glu Ala Lys Val Leu Cys Gln Ser Leu Gly Cys Gly Thr Ala Val
        275                 280                 285

Glu Arg Pro Lys Gly Leu Pro His Ser Leu Ser Gly Arg Met Tyr Tyr
    290                 295                 300

Ser Cys Asn Gly Glu Glu Leu Thr Leu Ser Asn Cys Ser Trp Arg Phe
305                 310                 315                 320

Asn Asn Ser Asn Leu Cys Ser Gln Ser Leu Ala Ala Arg Val Leu Cys
                325                 330                 335

Ser Ala Ser Arg Ser Leu His Asn Leu Ser Thr Pro Glu Val Pro Ala
            340                 345                 350

Ser Val Gln Thr Val Thr Ile Glu Ser Ser Val Thr Val Lys Ile Glu
        355                 360                 365

Asn Lys Glu Ser Arg
    370

<210> SEQ ID NO 4
<211> LENGTH: 1182
<212> TYPE: DNA
<213> ORGANISM: Homo sapiens

<400> SEQUENCE: 4
gagatacccg gccagacacc ctcacctgcg gtgcccagct gcccaggctg aggcaagaga      60
aggccagaaa ccatgcccat ggggtctctg caaccgctgg ccaccttgta cctgctgggg     120
atgctggtcg cttcctgcct cggacggctc agctggtatg acccagattt ccaggcaagg     180
ctcacccgtt ccaactcgaa gtgccagggc agctggagg tctacctcaa ggacggatgg     240
cacatggttt gcagccagag ctggggccgg agctccaagc agtgggagga ccccagtcaa     300
gcgtcaaaag tctgccagcg gctgaactgt ggggtgccct taagccttgg ccccttcctt     360
gtcacctaca cacctcagag ctcaatcatc tgctacggaa aactgggctc cttctccaac     420
tgcagccaca gcagaaatga catgtgtcac tctctgggcc tgacctgctt agaaccccag     480
aagacaacac ctccaacgac aaggcccccg cccaccacaa ctccagagcc acagctcct     540
cccaggctgc agctggtggc acagtctggc ggccagcact gtgccggcgt ggtggagttc     600
```

| | |
|---|---|
| tacagcggca gcctgggggg taccatcagc tatgaggccc aggacaagac ccaggacctg | 660 |
| gagaacttcc tctgcaacaa cctccagtgt ggctccttct tgaagcatct gccagagact | 720 |
| gaggcaggca gagcccaaga cccaggggag ccacgggaac accagccctt gccaatccaa | 780 |
| tggaagatcc agaactcaag ctgtacctcc ctggagcatt gcttcaggaa aatcaagccc | 840 |
| cagaaaagtg gccgagttct tgccctcctt tgctcaggtt ccagcccaa ggtgcagagc | 900 |
| cgtctggtgg ggggcagcag catctgtgaa ggcaccgtgg aggtgcgcca gggggctcag | 960 |
| tgggcagccc tgtgtgacag ctcttcagcc aggagctcgc tgcggtggga ggaggtgtgc | 1020 |
| cgggagcagc agtgtggcag cgtcaactcc tatcgagtgc tggacgctgg tgacccaaca | 1080 |
| tcccgggggc tcttctgtcc ccatcagaag ctgtcccagt gccacgaact ttgggagaga | 1140 |
| aattcctact gcaagaaggt gtttgtcaca tgccaggatt aa | 1182 |

<210> SEQ ID NO 5
<211> LENGTH: 1128
<212> TYPE: DNA
<213> ORGANISM: Homo sapiens

<400> SEQUENCE: 5

| | |
|---|---|
| gaccagctca acaccagcag tgcagagagt gagctctggg agccagggga gcggcttccg | 60 |
| gtccgtctga caaacgggag cagcagctgc agcgggacgg tggaggtgcg gctcgaggcg | 120 |
| tcctgggagc ccgcgtgcgg ggcgctctgg acagccgcg ccgccgaggc cgtgtgccga | 180 |
| gcactgggct gcggcgggc ggaggccgcc tctcagctcg ccccgccgac ccctgagctg | 240 |
| ccgcccccgc ctgcagccgg gaacaccagc gtagcagcta atgccactct ggccggggcg | 300 |
| cccgccctcc tgtgcagcgg cgccgagtgg cggctctgcg aggtggtgga gcacgcgtgc | 360 |
| cgcagcgacg ggaggcgggc ccgtgtcacc tgtgcagaga accgcgcgct gcgcctggtg | 420 |
| gacggtggcg gcgcctgcgc cggccgcgtg gagatgctgg agcatggcga gtggggatca | 480 |
| gtgtgcgatg acacttggga cctggaggac gcccacgtgg tgtgcaggca actgggctgc | 540 |
| ggctgggcag tccaggccct gccggcttg cacttcacgc ccggccgcgg gcctatccac | 600 |
| cgggaccagg tgaactgctc gggggccgaa gcttacctgt gggactgccc ggggctgcca | 660 |
| ggacagcact actgcggcca caagaggac gcgggcgtgg tgtgctcaga gcaccagtcc | 720 |
| tggcgcctga caggggcgc tgaccgctgc gagggcagg tggaggtaca cttccgaggg | 780 |
| gtctggaaca cagtgtgtga cagtgagtgg taccatcgg aggccaaggt gctctgccag | 840 |
| tccttgggct gtggaactgc ggttgagagg cccaagggc tgccccactc cttgtccggc | 900 |
| aggatgtact actcatgcaa tggggaggag ctcaccctct ccaactgctc ctggcggttc | 960 |
| aacaactcca acctctgcag ccagtcgctg cagccaggg tcctctgctc agcttcccgg | 1020 |
| agtttgcaca atctgtccac tcccgaagtc cctgcaagtg ttcagacagt cactatagaa | 1080 |
| tcttctgtga cagtgaaaat agagaacaag gaatctcggt agggatcc | 1128 |

<210> SEQ ID NO 6
<211> LENGTH: 21
<212> TYPE: DNA
<213> ORGANISM: Artificial
<220> FEATURE:
<223> OTHER INFORMATION: Forward primer for PCR amplification of human CD5.

<400> SEQUENCE: 6

| | |
|---|---|
| gctgtcccag tgccacgaac t | 21 |

<210> SEQ ID NO 7
<211> LENGTH: 21
<212> TYPE: DNA
<213> ORGANISM: Artificial
<220> FEATURE:
<223> OTHER INFORMATION: Reverse primer PCR amplification of human CD5

<400> SEQUENCE: 7
gaagctcctc tgtgtcctca t                                              21

<210> SEQ ID NO 8
<211> LENGTH: 22
<212> TYPE: DNA
<213> ORGANISM: Artificial
<220> FEATURE:
<223> OTHER INFORMATION: Forward primer PCR amplification of house-
      keeping LIEX gene

<400> SEQUENCE: 8
tcactcaagg caaccttcct gc                                             22

<210> SEQ ID NO 9
<211> LENGTH: 25
<212> TYPE: DNA
<213> ORGANISM: Artificial
<220> FEATURE:
<223> OTHER INFORMATION: Reverse primer PCR amplification of
      house-keeping LIEX gene

<400> SEQUENCE: 9
cgacctcatc tctaaccatg aacag                                          25

<210> SEQ ID NO 10
<211> LENGTH: 268
<212> TYPE: DNA
<213> ORGANISM: Simian virus 40

<400> SEQUENCE: 10
gtgtggaaag tccccaggct ccccagcagg cagaagtatg caaagcatgc atctcaatta    60
gtcagcaacc aggtgtggaa agtccccagg ctccccagca ggcagaagta tgcaaagcat   120
gcatctcaat tagtcagcaa ccatagtccc gcccctaact ccgcccatcc cgcccctaac   180
tccgcccagt tccgcccatt ctccgcccca tggctgacta ttttttttta tttatgcaga   240
ggccgaggcc gcctcggcct ctgagcta                                      268

<210> SEQ ID NO 11
<211> LENGTH: 31
<212> TYPE: DNA
<213> ORGANISM: Artificial
<220> FEATURE:
<223> OTHER INFORMATION: Forward primer PCR amplification of human CD6
      ectodomain (extracellular portion)

<400> SEQUENCE: 11
cttctagatg accagctcaa caccaccagc a                                   31

<210> SEQ ID NO 12
<211> LENGTH: 33
<212> TYPE: DNA
<213> ORGANISM: Artificial
<220> FEATURE:
<223> OTHER INFORMATION: Reverse primer for PCR amplification of human
      CD6 ectodomain (extracellular portion)

<400> SEQUENCE: 12
gcggatccct attctatagt gactgtctga aca                33

<210> SEQ ID NO 13
<211> LENGTH: 369
<212> TYPE: PRT
<213> ORGANISM: Homo sapiens

<400> SEQUENCE: 13

Met Pro Met Gly Ser Leu Gln Pro Leu Ala Thr Leu Tyr Leu Leu Gly
1               5                   10                  15

Met Leu Val Ala Ser Cys Leu Gly Arg Leu Ser Trp Tyr Asp Pro Asp
                20                  25                  30

Phe Gln Ala Arg Leu Thr Arg Ser Asn Ser Lys Cys Gln Gly Gln Leu
                35                  40                  45

Glu Val Tyr Leu Lys Asp Gly Trp His Met Val Cys Ser Gln Ser Trp
    50                  55                  60

Gly Arg Ser Ser Lys Gln Trp Glu Asp Pro Ser Gln Ala Ser Lys Val
65                  70                  75                  80

Cys Gln Arg Leu Asn Cys Gly Val Pro Leu Ser Leu Gly Pro Phe Leu
                85                  90                  95

Val Thr Tyr Thr Pro Gln Ser Ser Ile Ile Cys Tyr Gly Gln Leu Gly
                100                 105                 110

Ser Phe Ser Asn Cys Ser His Ser Arg Asn Asp Met Cys His Ser Leu
                115                 120                 125

Gly Leu Thr Cys Leu Glu Pro Gln Lys Thr Thr Pro Thr Thr Arg
        130                 135                 140

Pro Pro Pro Thr Thr Thr Pro Glu Pro Thr Ala Pro Pro Arg Leu Gln
145                 150                 155                 160

Leu Val Ala Gln Ser Gly Gly Gln His Cys Ala Gly Val Val Glu Phe
                165                 170                 175

Tyr Ser Gly Ser Leu Gly Gly Thr Ile Ser Tyr Glu Ala Gln Asp Lys
                180                 185                 190

Thr Gln Asp Leu Glu Asn Phe Leu Cys Asn Asn Leu Gln Cys Gly Ser
        195                 200                 205

Phe Leu Lys His Leu Pro Glu Thr Glu Ala Gly Arg Ala Gln Asp Pro
210                 215                 220

Gly Glu Pro Arg Glu His Gln Pro Leu Pro Ile Gln Trp Lys Ile Gln
225                 230                 235                 240

Asn Ser Ser Cys Thr Ser Leu Glu His Cys Phe Arg Lys Ile Lys Pro
                245                 250                 255

Gln Lys Ser Gly Arg Val Leu Ala Leu Leu Cys Ser Gly Phe Gln Pro
                260                 265                 270

Lys Val Gln Ser Arg Leu Val Gly Gly Ser Ser Ile Cys Glu Gly Thr
                275                 280                 285

Val Glu Val Arg Gln Gly Ala Gln Trp Ala Ala Leu Cys Asp Ser Ser
        290                 295                 300

Ser Ala Arg Ser Ser Leu Arg Trp Glu Glu Val Cys Arg Glu Gln Gln
305                 310                 315                 320

Cys Gly Ser Val Asn Ser Tyr Arg Val Leu Asp Ala Gly Asp Pro Thr
                325                 330                 335

Ser Arg Gly Leu Phe Cys Pro His Gln Lys Leu Ser Gln Cys His Glu
                340                 345                 350

Leu Trp Glu Arg Asn Ser Tyr Cys Lys Lys Val Phe Val Thr Cys Gln
            355                 360                 365

```
Asp

<210> SEQ ID NO 14
<211> LENGTH: 24
<212> TYPE: PRT
<213> ORGANISM: Homo sapiens

<400> SEQUENCE: 14

Met Pro Met Gly Ser Leu Gln Pro Leu Ala Thr Leu Tyr Leu Leu Gly
1               5                   10                  15

Met Leu Val Ala Ser Cys Leu Gly
            20
```